(12) United States Patent
Moroi et al.

(10) Patent No.: US 8,992,079 B2
(45) Date of Patent: Mar. 31, 2015

(54) TEMPERATURE MEASUREMENT APPARATUS, METHOD OF ESTIMATING TEMPERATURE PROFILE, RECORDING MEDIUM AND HEAT TREATMENT APPARATUS

(75) Inventors: Masayuki Moroi, Yamanashi (JP); Hitoshi Kikuchi, Iwate (JP); Masato Koakutsu, Iwate (JP)

(73) Assignee: Tokyo Electron Limited, Tokyo (JP)

( * ) Notice: Subject to any disclaimer, the term of this patent is extended or adjusted under 35 U.S.C. 154(b) by 575 days.

(21) Appl. No.: 13/478,304

(22) Filed: May 23, 2012

(65) Prior Publication Data
US 2013/0130187 A1    May 23, 2013

(30) Foreign Application Priority Data
May 26, 2011   (JP) .................................. 2011-118372

(51) Int. Cl.
| | |
|---|---|
| G01K 1/14 | (2006.01) |
| G01K 13/08 | (2006.01) |
| H01L 21/00 | (2006.01) |
| G01N 25/00 | (2006.01) |
| F27D 21/00 | (2006.01) |
| H01L 21/67 | (2006.01) |
| H01L 21/687 | (2006.01) |
| F27D 19/00 | (2006.01) |
| F27B 17/00 | (2006.01) |

(52) U.S. Cl.
CPC ................ *G01N 25/00* (2013.01); *F27D 21/00* (2013.01); *F27B 17/0025* (2013.01); *H01L 21/67248* (2013.01); *H01L 21/68764* (2013.01); *H01L 21/68771* (2013.01); *F27D 19/00* (2013.01); *F27D 2019/0025* (2013.01)

USPC ...... 374/153; 374/141; 374/178; 324/207.25; 702/130; 432/32; 438/14

(58) Field of Classification Search
USPC ......... 374/178, 141, 100, 153, 208, 137, 166, 374/167, 120, 121; 324/207.11, 207.12, 324/207.25, 750.13, 750.16, 750.22, 324/754.08, 754.09; 438/14, 795, 799; 702/94, 130; 432/32
See application file for complete search history.

(56) References Cited

U.S. PATENT DOCUMENTS

| | | | | |
|---|---|---|---|---|
| 4,828,224 | A | * | 5/1989 | Crabb et al. ................... 251/298 |
| 5,117,769 | A | * | 6/1992 | deBoer et al. ................. 118/666 |

(Continued)

FOREIGN PATENT DOCUMENTS

| | | |
|---|---|---|
| JP | 11-106289 | 4/1999 |
| KR | 2007031567 A * | 3/2007 |

*Primary Examiner* — Gail Kaplan Verbitsky
(74) *Attorney, Agent, or Firm* — IPUSA, PLLC

(57) ABSTRACT

A temperature measurement apparatus for estimating a temperature profile in a process container, includes a radiation temperature measurement unit configured to measure the temperature of plural temperature measurement areas at a surface of the rotating table in a radius direction of the rotating table by scanning the surface of the rotating table in the radius direction; an operation control unit that controls to start heating of the process container by a heater while keeping the rotating table immobilized, and controls to repeat a scanning operation, in which the radiation temperature measurement unit scans the surface of the rotating table in the radius direction to obtain the temperature of the plural temperature measurement areas while the rotating table is rotated in a circumferential direction of the rotating table, after a predetermined period has passed from starting the heating of the process container.

10 Claims, 16 Drawing Sheets

(56) References Cited

U.S. PATENT DOCUMENTS

| | | | |
|---|---|---|---|
| 6,064,799 A * | 5/2000 | Anderson et al. | 392/416 |
| 6,164,816 A * | 12/2000 | Aderhold et al. | 374/1 |
| 6,538,425 B1 * | 3/2003 | Kawada | 324/750.22 |
| 6,634,245 B1 * | 10/2003 | Yoshioka et al. | 73/865.8 |
| 6,770,852 B1 * | 8/2004 | Steger | 219/390 |
| 7,271,604 B2 * | 9/2007 | Reitinger | 324/750.03 |
| 8,573,836 B2 * | 11/2013 | Sasaki et al. | 374/141 |
| 2002/0039030 A1 * | 4/2002 | Khazei | 324/750 |
| 2003/0047559 A1 * | 3/2003 | Watanabe et al. | 219/711 |
| 2010/0000855 A1 * | 1/2010 | Nakamura et al. | 204/192.12 |
| 2010/0170435 A1 * | 7/2010 | Franken et al. | 118/666 |
| 2012/0221167 A1 * | 8/2012 | Hong | 700/300 |
| 2012/0303313 A1 * | 11/2012 | Moroi et al. | 702/134 |
| 2013/0052754 A1 * | 2/2013 | Zaitsu et al. | 438/5 |
| 2013/0224675 A1 * | 8/2013 | Park | 432/253 |
| 2014/0174351 A1 * | 6/2014 | Aikawa | 118/713 |
| 2014/0301010 A1 * | 10/2014 | Hayahara et al. | 361/234 |

* cited by examiner

TEMPERATURE MEASUREMENT APPARATUS, METHOD OF ESTIMATING TEMPERATURE PROFILE, RECORDING MEDIUM AND HEAT TREATMENT APPARATUS

BACKGROUND OF THE INVENTION

1. Field of the Invention

The present invention relates to a temperature measurement apparatus used for a heat treatment apparatus that performs a heat treatment to a substrate while rotating the substrate by rotating a rotating table, a method of estimating a temperature profile, a recording medium and a heat treatment apparatus.

2. Description of the Related Art

For a heat treatment apparatus, an apparatus including a process container, in which a rotating table is provided, is known. In this heat treatment apparatus, plural semiconductor wafers (which are examples of substrates, and hereinafter simply referred to as wafers) are mounted on the rotating table along a rotating direction. Further in this heat treatment apparatus, a gas supply unit that supplies process gas is provided to extend in a radius direction of the rotating table. Further, within this heat treatment apparatus, a heater for heating the wafers is provided and layers are deposited on the wafers by discharging the gas from the gas supply unit while the wafers are heated and the rotating table is rotated.

For example, when developing the heat treatment apparatus, a test for grasping a temperature profile in the process container is performed. For this test, thermocouples are attached to components in the process container and a temperature around the thermocouples is measured after the heater is switched on. Here, as each of the thermocouples can only measure the temperature in the vicinity, the temperature profile in the process container is estimated based on the temperature measured by the thermocouples.

However, when performing this test, it is necessary to open the process container for attaching the thermocouples. Therefore, a lot of operation time is necessary for a preparation for the test. Further, as the temperature profile in the process container is estimated based on the temperature measured by the limited number of thermocouples provided in the process container, there remains an anxiety that an accurate temperature profile cannot be estimated.

Patent Document 1 discloses a method of measuring a temperature profile of a surface of a substrate which is mounted on a rotary susceptor provided in a reactor for vapor deposition of a thin layer. In this method, the temperature profile of the surface of the substrate is measured by continuously measuring temperature of the surface of the substrate mounted on the rotary susceptor by a temperature measurement unit provided at a predetermined position, analyzing a path of measured points of the substrate, which vary in accordance with a rotation of the susceptor, based on information of a rotating speed of the susceptor, and coordinating the temperature measured by the temperature measurement unit with the measured points of the substrate based on the analyzed path.

PATENT DOCUMENT

[Patent Document 1] Japanese Laid-open Patent Publication No. H11-106289

SUMMARY OF THE INVENTION

The present invention is made in light of the above problems, and provides a technique to easily and accurately estimate a temperature profile in a process container, including a rotating table capable of being rotated and on which a substrate is mounted, of a heat treatment apparatus.

According to an embodiment, there is provided a temperature measurement apparatus for estimating a temperature profile in a process container of a heat treatment apparatus including the process container, in which a rotating table for mounting a substrate is provided, and a heater for heating the process container, including, a radiation temperature measurement unit configured to measure the temperature of plural temperature measurement areas at a surface of the rotating table in a radius direction of the rotating table by scanning the surface of the rotating table in the radius direction; an instruction receiving unit that receives an instruction for measuring the temperature profile in the process container; an operation control unit that controls to start heating of the process container by the heater while keeping the rotating table immobilized, when the instruction receiving unit receives the instruction for measuring the temperature profile in the process container, and controls to repeat a scanning operation, in which the radiation temperature measurement unit scans the surface of the rotating table in the radius direction to obtain the temperature of the plural temperature measurement areas in the radius direction while the rotating table is rotated in a circumferential direction of the rotating table with respect to the radiation temperature measurement unit, after a predetermined period has passed from starting the heating of the process container, for obtaining the temperature of the plural temperature measurement areas at the surface of the rotating table in the radius direction and the circumferential direction from the radiation temperature measurement unit; a temperature map generating unit that specifies the address of the temperature measurement area for which the operation control unit obtains the temperature based on the number of the temperature measurement areas obtained by the radiation temperature measurement unit for each of the scanning operations in the radius direction of the rotating table, and the rotating speed of the rotating table, and stores the temperature in correspondence with the corresponding address in a storing unit; and a temperature data display processing unit that displays the temperature profile of the surface of the rotating table based on the temperature and the address stored in the storing unit by the temperature map generating unit, as the temperature profile in the process container.

According to another embodiment, there is provided a heat treatment apparatus, including, the process container in which the rotating table for mounting the substrate is provided; the heater that heats the process container; and the above temperature measurement apparatus.

According to another embodiment, there is provided a method of estimating a temperature profile in a process container of a heat treatment apparatus including the process container, in which a rotating table for mounting a substrate is provided, and a heater for heating the process container, including, starting heating of the process container by the heater while keeping the rotating table immobilized, based on an instruction for measuring the temperature profile in the process container; after a predetermined period has passed from starting the heating of the process container, repeating a scanning operation, in which a radiation temperature measurement unit, which is configured to measure temperature of plural temperature measurement areas at a surface of the rotating table in a radius direction of the rotating table by scanning the surface of the rotating table in the radius direction, scans the surface of the rotating table in the radius direction to obtain the temperature of the plural temperature measurement areas in the radius direction while the rotating table is rotated in a circumferential direction of the rotating table with respect to the radiation temperature measurement unit; specifying the address of the temperature measurement area for which the temperature is obtained based on the number of the temperature measurement areas obtained by the radiation temperature measurement unit for each of the scanning operations in the radius direction of the rotating table, and the rotating speed of the rotating table; storing the temperature in correspondence with the corresponding address in a storing unit; and displaying the temperature profile of the surface of the rotating table based on the temperature and the address stored in the storing unit, as the temperature profile in the process container.

According to another embodiment, there is provided a non-transitory computer-readable recording medium having recorded thereon a program that causes a computer to execute the above method of estimating a temperature profile.

BRIEF DESCRIPTION OF THE DRAWINGS

Other objects, features and advantages of the present invention will become more apparent from the following detailed description when read in conjunction with the accompanying drawings.

DETAILED DESCRIPTION OF THE PREFERRED EMBODIMENTS

Figure 1:
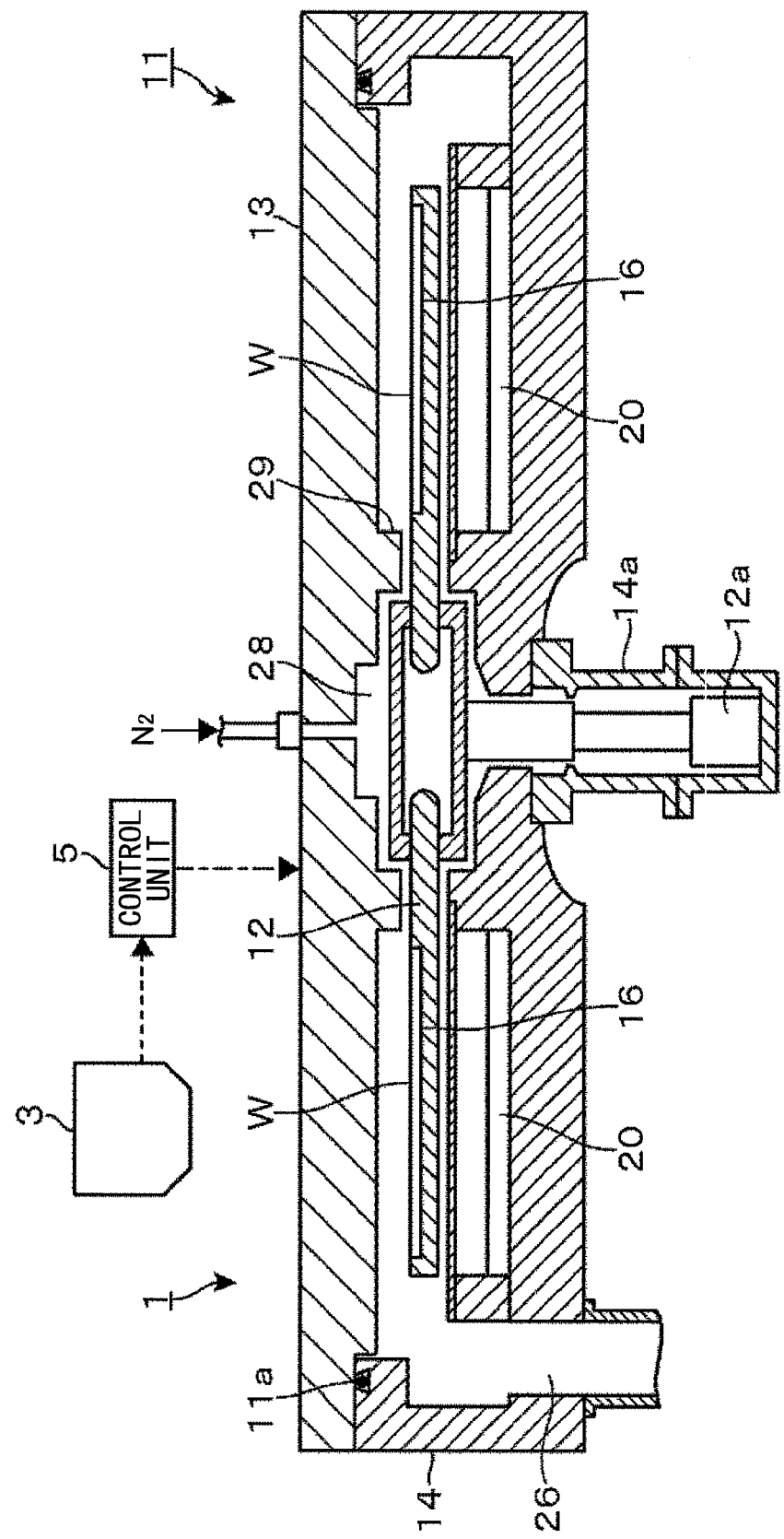
FIG. 1 is a cross-sectional view of a film deposition apparatus of an embodiment.

The invention will be described herein with reference to illustrative embodiments. Those skilled in the art will recognize that many alternative embodiments can be accomplished using the teachings of the present invention and that the invention is not limited to the embodiments illustrated for explanatory purposes.

It is to be noted that, in the explanation of the drawings, the same components are given the same reference numerals, and explanations are not repeated.

First, a film deposition apparatus 1 (a heat treatment apparatus) in which a temperature measurement apparatus is incorporated is explained. The film deposition apparatus 1 performs Atomic Layer Deposition (ALD) and Molecular Layer Deposition (MLD) onto a semiconductor wafer (which is a substrate, and hereinafter simply referred to as a wafer) W.

Figure 2:
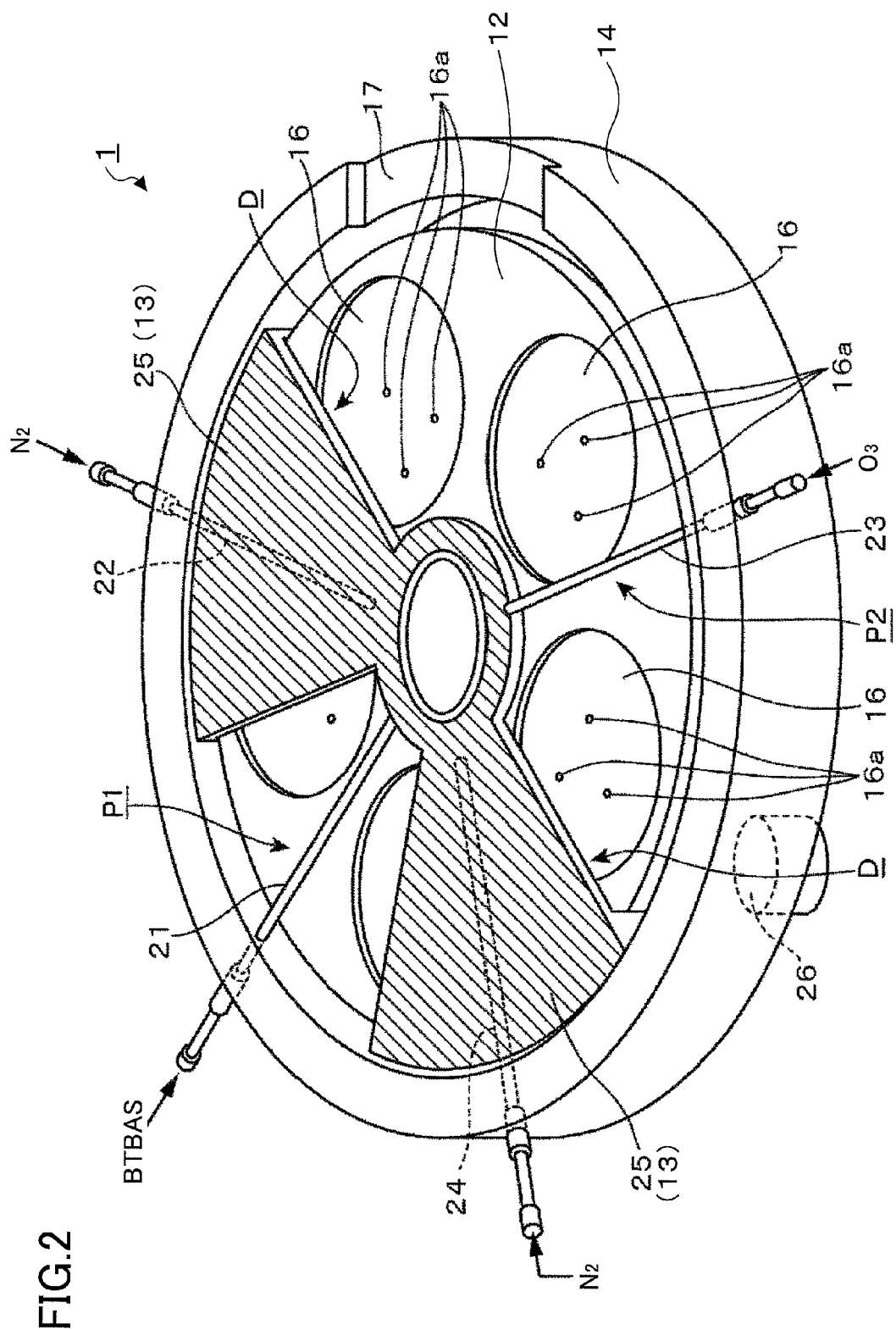
FIG. 2 is a perspective view of the film deposition apparatus.
Figure 3:
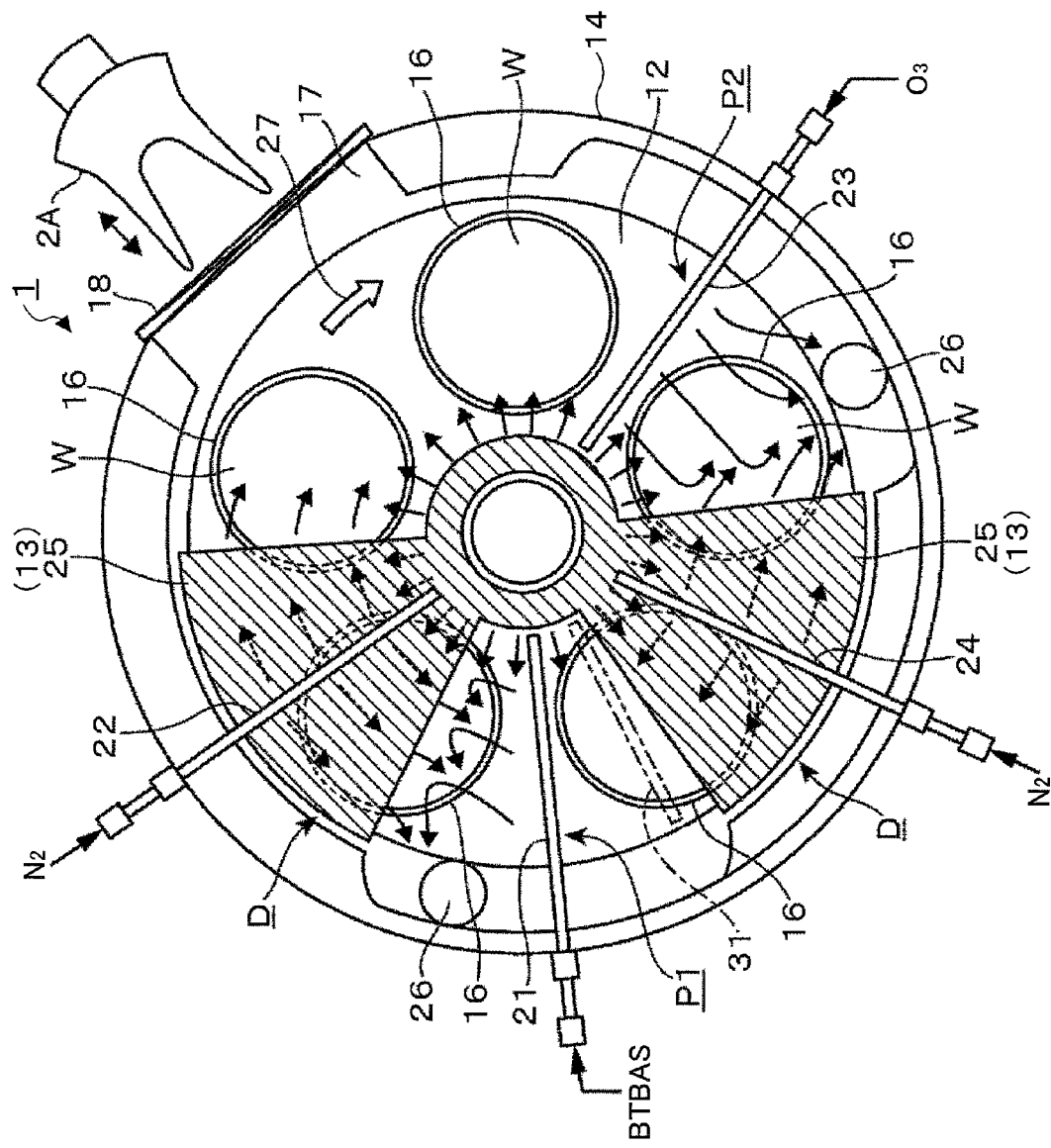
FIG. 3 is a cross-sectional view of a vacuum chamber of the film deposition apparatus taken along a horizontal plane.

FIG. 1 is a cross-sectional view, FIG. 2 is a perspective view, and FIG. 3 is a cross-sectional view taken along a horizontal plane, of the film deposition apparatus 1.

The film deposition apparatus 1 includes a substantially flat circular vacuum chamber 11 (process container), a rotating table 12, a transferring mechanism 2A (see FIG. 3), a rotation drive mechanism 12a, a heater 20, a first reactant gas nozzle 21, a separation gas nozzle 22, a second reactant gas nozzle 23, a separation gas nozzle 24 (see FIG. 2 and FIG. 3), a radiation temperature measurement unit 3 and a control unit 5. Here, the radiation temperature measurement unit 3 and the control unit 5 compose a temperature measurement apparatus.

The rotation drive mechanism 12a rotates the rotating table 12 in a circumferential direction. The transferring mechanism 2A transfers the wafer W. The heater 20 is provided below the rotating table 12.

The vacuum chamber 11 includes a top plate 13 and a container body 14 which composes a side wall and a bottom portion of the vacuum chamber 11. The vacuum chamber 11 is provided in atmosphere, and is configured to keep the inside airtight. The vacuum chamber 11 includes a seal member 11a for keeping the vacuum chamber 11 airtight (see FIG. 1), a cover 14a that blocks a center portion of the container body 14, exhaust ports 26, a transferring port 17 (see FIG. 2 and FIG. 3), and a shutter 18 (see FIG. 3) capable of opening and closing the transferring port 17.

The structure and the operation in heat treatment (deposition of film) of the film deposition apparatus 1 is explained.

The rotating table 12 is horizontally provided in the vacuum chamber 11. The rotating table 12 is provided with five concave portions 16 at its surface along a rotation direction (the circumferential direction) for mounting the wafers W.

As shown in FIG. 3, when the transferring mechanism 2A proceeds into the vacuum chamber 11 from the transferring port 17 while holding a wafer W, elevating pins (not shown in the drawings) are protruded above the rotating table 12 from holes 16a in the concave portion 16, which is positioned to correspond to the transferring port 17, to hold the wafer W transferred by the transferring mechanism 2A. With this, the wafer W is transferred from the transferring mechanism 2A to the concave portion 16 via the elevating pins.

Such a series of operations by the transferring mechanism 2A, the elevating pins and the rotating table 12 are repeated so that wafers W are passed to each of the concave portions 16, respectively.

Then, for example, when the process of the wafers W is finished so that the wafers W are carried out from the vacuum chamber 11, the elevating pins (not shown in the drawings) raise the wafer W in the concave portion 16, which is positioned to correspond to the transferring port 17. Then, the transferring mechanism 2A receives the raised wafer W to carry it outside the vacuum chamber 11.

The first reactant gas nozzle 21, the separation gas nozzle 22, the second reactant gas nozzle 23 and the separation gas nozzle 24 formed in bars and extending from an outer periphery to the center of the rotating table 12, respectively, are provided on the rotating table 12 in this order in the circumferential direction. The gas nozzles 21 to 24 have open ports and supply gas along a radius of the rotating table 12, respectively. In this embodiment, for example, the first reactant gas nozzle 21 outputs bistertialbutylaminosilane (BTBAS) gas as the first reactant gas, the second reactant gas nozzle 23 outputs $O_3$ (ozone) gas as second reactant gas, respectively. The separation gas nozzles 22 and 24 output $N_2$ (nitrogen) gas as separation gas, respectively.

The top plate 13 of the vacuum chamber 11 is provided with two fan-shaped protruding portions 25 protruding downward which are provided with a space therebetween in the circumferential direction. The separation gas nozzles 22 and 24 are embedded in the protruding portions 25 respectively so as to divide the corresponding protruding portion 25 in the circumferential direction. The first reactant gas nozzle 21 and the second reactant gas nozzle 23 are provided to be apart from the protruding portions 25.

The exhaust ports 26 are provided at a bottom surface of the container body 14 to be open at the outer periphery of the rotating table 12.

When wafers W are mounted on the concave portions 16 of the rotating table 12, the vacuum chamber 11 is evacuated from the exhaust ports 26 to be a vacuum. Then, the wafers W are heated to be 350° C., for example, by the heater 20 via the rotating table 12 while the rotating table 12 is being rotated. An arrow 27 shown in FIG. 3 shows the rotating direction of the rotating table 12.

Subsequently, the gas is supplied from the gas nozzles 21 to 24, respectively, and the wafers W alternately pass through a first processing area P1 under the first reactant gas nozzle 21 and a second processing area P2 under the second reactant gas nozzle 23. With this operation, BTBAS gas and subsequently $O_3$ gas are adsorbed on the wafers W. Therefore, BTBAS molecules deposited on the wafers W are oxidized to foam a single or plural of silicon oxide molecular layer(s), respectively. Then, the silicon oxide molecular layers are stacked in order so that a silicon oxide layer with a predetermined thickness is formed on each of the wafers W.

When depositing layers, $N_2$ gas which is the separation gas supplied to the separation areas D from the nozzles 22 and 24 spreads in the separation areas D in the circumferential direction to prevent mixing of BTBAS gas and $O_3$ gas on the gas rotating table 12 and flow excess BTBAS gas and $O_3$ gas toward the exhaust ports 26. Further, when depositing layers, $N_2$ gas is supplied to a space 28 above the center portion of the rotating table 12. The $N_2$ gas supplied to the space 28 is further supplied to the outer periphery of the rotating table 12 in the radius direction through a lower portion of a protruding portion 29 in a ring-form which protrudes downward. Thus, BTBAS gas and $O_3$ gas in the center portion can be prevented from being mixed. In FIG. 3, flows of each of the gas when depositing layers are expressed by arrows. Further, although not shown in the drawings, $N_2$ gas is also supplied into the cover 14a and to a back surface side of the rotating table 12 to purge the reactant gas.

Then, a method of measuring a temperature profile in the vacuum chamber 11 by the radiation temperature measurement unit 3 of the film deposition apparatus 1 of the embodiment is explained.

Figure 4:
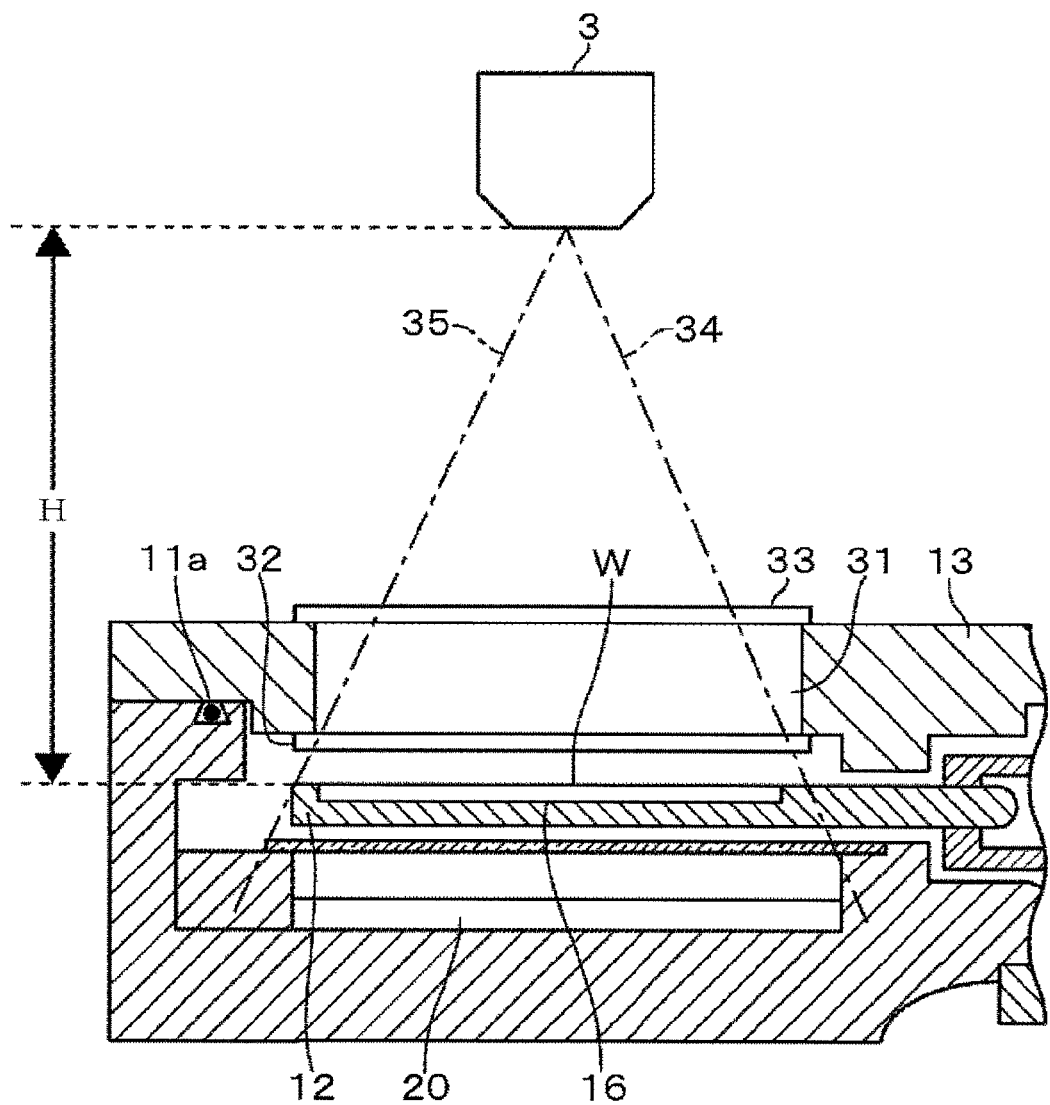
FIG. 4 is a view for explaining a temperature measurement area of a temperature measurement unit.

FIG. 4 is a cross-sectional view partially showing the top plate 13 and the rotating table 12. The explanation is made with reference to FIG. 4 as well. FIG. 4 corresponds to a cross-sectional view taken along a slit 31 shown as a chain line between the gas nozzle 21 and the separation gas nozzle 24 in FIG. 3.

The top plate 13 is provided with the slit 31 which is opened at a position shown by the chain line in FIG. 3 to be extended in the radius direction of the rotating table 12. The slit 31 is provided to correspond to at least a diameter of each of the concave portions 16 provided in the rotating table 12, in the radius direction. The slit 31 may be provided to correspond to a radius of the rotating table 12 in the radius direction.

The film deposition apparatus 1 further includes a lower transparent plate 32 and an upper transparent plate 33 which are provided to cover the slit 31 at the upper side and the lower side, respectively. The lower transparent plate 32 and the upper transparent plate 33 are made of a material which is capable of transmitting an infrared ray radiated from the surface of the rotating table 12 as well as capable of keeping inside the vacuum chamber 11 airtight, such as sapphire or the like, for example. With this structure, the radiation temperature measurement unit 3 can measure the temperature of the surface of the rotating table 12. Therefore, in this embodiment, the temperature of the surface of the rotating table 12 can be measured while keeping the vacuum chamber 11 airtight.

The radiation temperature measurement unit 3 is a noncontact thermometer. The radiation temperature measurement unit 3 is provided above the slit 31. In this embodiment, a height "H", shown in FIG. 4, from the surface of the rotating table 12 to a lower end of the radiation temperature measurement unit 3 may be 500 mm, for example. In this embodiment, the radiation temperature measurement unit 3 is configured to be capable of scanning the surface of the rotating table 12 in the radius direction of the rotating table 12 for measuring temperature of plural positions of the rotating table 12 along the radius direction.

Figure 5:
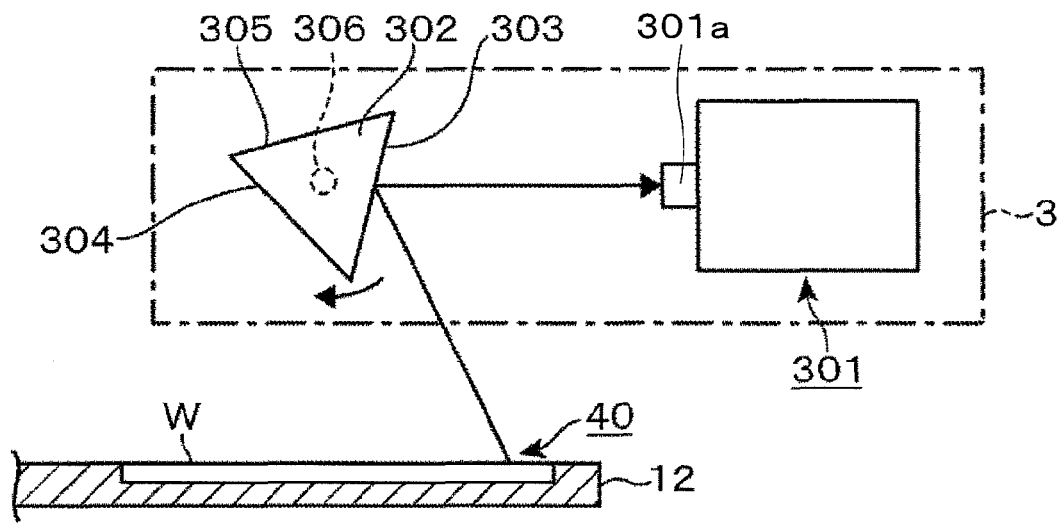
FIG. 5 is a schematic view of the temperature measurement unit.
Figure 6:
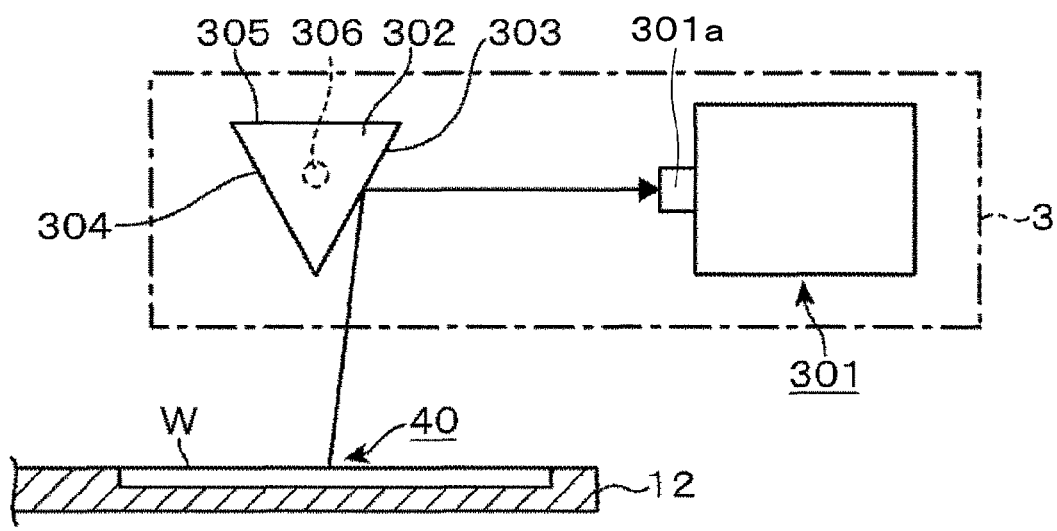
FIG. 6 is a schematic view of the temperature measurement unit.
Figure 7:
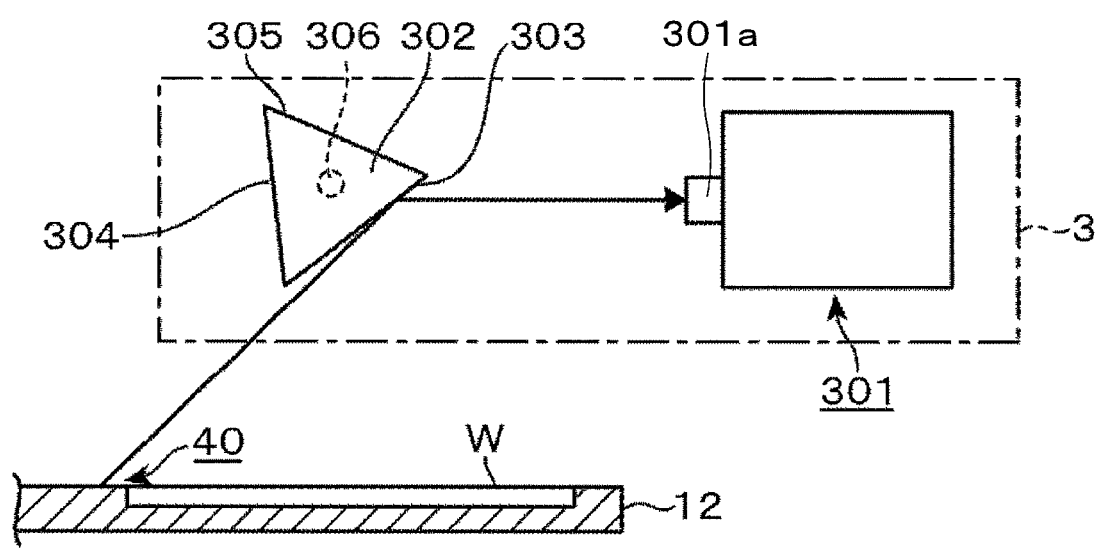
FIG. 7 is a schematic view of the temperature measurement unit.

FIG. 5 to FIG. 7 show schematic views of the radiation temperature measurement unit 3.

The radiation temperature measurement unit 3 includes a rotating body 302 including reflection planes 303 to 305 and a detection unit 301 including a light receiver 301a that receives the infrared ray.

The detection unit 301 is an infrared ray sensor that receives the infrared ray, and calculates a measured temperature value based on the amount of the received infrared ray. In this embodiment, the light receiver 301a of the detection unit 301 receives the infrared ray which is reflected by either of the reflection planes 303 to 305 of the rotating body 302.

In this embodiment, the rotating body 302 is formed to be a triangle in a plane view where three surfaces of the triangle function as the reflection planes 303 to 305, respectively. As shown in FIG. 5, the rotating body 302 is rotated in a direction shown by an arrow while having a rotating shaft 306 as the center of rotation. Here, the rotating body 302 may be, for example, composed of a servomotor which rotates at a predetermined speed, 50 Hz, for example.

Each of the reflection planes 303 to 305 of the rotating body 302 are configured to be capable of reflecting the infrared ray radiated from the surface of the rotating table 12 under the slit 31 of the top plate 13 when the corresponding reflection plane (303 to 305) is positioned to face the light receiver 301a of the detection unit 301.

The detection unit 301 is configured and placed such that the light receiver 301a is capable of receiving the infrared ray reflected by either of the reflection planes 303 to 305 of the rotating body 302.

With this structure, the infrared ray, radiated from an area on the rotating table 12 which is determined by a relative position between one of the reflection planes 303 to 305 which is positioned to face the light receiver 301a of the detection unit 301 and the light receiver 301a of the detection unit 301, is received by the light receiver 301a of the detection unit 301. This area on the rotating table 12 is referred to as a temperature measurement area 40, hereinafter. For an example shown in FIG. 5 to FIG. 7, the reflection plane 303 of the rotating body 302 is positioned to face the light receiver 301a of the detection unit 301. Thus, an area at the surface of the rotating table 12 which is reflected by a portion, positioned at the same height as the light receiver 301a, of the reflection plane 303 is determined as the temperature measurement area 40.

The detection unit 301 calculates a measured temperature value which is in accordance with the received amount of the infrared ray based on the received amount of the infrared ray. The measured temperature value calculated by the detection unit 301 is sequentially sent to the control unit 5 (FIG. 1).

Further in this embodiment, the rotating body 302 is configured such that when each of the reflection planes 303 to 305 is placed to face the light receiver 301a of the detection unit 301, the temperature measurement area 40 which is reflected by the corresponding reflection plane (303, 304 or 305) moves from an inner side to an outer side of the surface of the rotating table 12 in the radius direction. It means that, in this embodiment, each of the reflection planes 303 to 305 of the rotating body 302 are structured to correspond to a length of the rotating table 12 between the inner side to the outer side in the radius direction. With this structure, regular and continuous scanning from the inner side to the outer side of the rotating table 12 in the radius direction can be performed. Therefore, high-speed scanning can be possible. Further, as the scanning can be performed at a high speed, the scanning from the inner side to the outer side of the rotating table 12 in the radius direction can be performed regardless of the rotation speed of the rotating table 12. Therefore, it is possible to appropriately measure the temperature of the surface of the rotating table 12 in all cases such as when the rotating table 12 is immobilized, when the rotating table 12 is rotated at a low speed, and when the rotating table 12 is rotated at a high speed.

Further, although the rotating body 302 is formed to be a triangle in a plane view in this embodiment, the rotating body 302 may be formed to be a polygon, other than a triangle, provided that each of the reflection planes of the rotating body 302 are structured to correspond to the length of the rotating table 12 between the inner side to the outer side in the radius direction.

As shown in FIG. 5, the reflection plane 303 is being positioned to face the light receiver 301a of the detection unit 301. Under this state, when the rotating body 302 is rotated around the rotating shaft 306, the angle between a surface of the reflection plane 303 and the surface of the rotating table 12 generally changes as shown in FIG. 6 and FIG. 7 so that the temperature measurement area 40 at the surface of the rotating table 12, including the wafers W, shifts from the inner side (right-side in FIG. 5 to FIG. 7) to the outer side (left-side in FIG. 5 to FIG. 7) of the rotating table 12. Then, when the temperature measurement area 40 at the surface of the rotating table 12 reaches the most outer side of the rotating table 12, the interface between the reflection plane 303 and the reflection plane 305 is positioned to be the same height as the light receiver 301a. Subsequently, the reflection plane that is positioned to face the light receiver 301a of the detection unit 301 changes from the reflection plane 303 to the reflection plane 305 so that the angle between a surface of the reflection plane (303 or 305) and the surface of the rotating table 12 suddenly changes. Therefore, the temperature measurement area 40 at the surface of the rotating table 12 is moved to the inner side again.

When the rotating body 302 is rotated around the rotating shaft 306 under this state, the temperature measurement area 40 at the surface of the rotating table 12 shifts from the inner side to the outer side of the rotating table 12 in the radius direction again. In this embodiment, repeating this operation, the radiation temperature measurement unit 3 can continuously and repeatedly perform the scanning from the inner side to the outer side of the rotating table 12 in the radius direction.

Further, the detection unit 301 is configured such that temperature of 128 areas on the surface of the rotating table 12 in the radius direction can be obtained by continuously absorbing the infrared ray 128 times from each of the reflection planes 303 to 305 of the rotating body 302 while the rotating body 302 is being rotated. This means that the detection unit 301 is configured to measure the temperature of 128 of the temperature measurement areas 40 in a single scanning operation.

In this embodiment, when the rotating body 302 is composed of a servomotor which rotates at 50 Hz as described above, for example, as the rotating body 302 includes three reflection planes 303 to 305, the scanning speed of the radiation temperature measurement unit 3 from the inner side to the outer side of the rotating table 12 becomes 150 Hz. This means that the radiation temperature measurement unit 3 can perform the scanning 150 times per second.

Further, the radiation temperature measurement unit 3 may be configured to have a diameter of the temperature measurement area 40 become 5 mm, for example.

The radiation temperature measurement unit 3 may be configured to be capable of scanning a range at the rotating table 12 from the inner side of the concave portions 16 to an end of the outer periphery of the rotating table 12. Chain lines 34 and 35 in FIG. 4 show infrared rays to the radiation temperature measurement unit 3 radiated from the temperature measurement area 40 at the most inner side and at the most outer periphery side of the rotating table 12, respectively.

In this embodiment, the rotating table 12 is rotated while the radiation temperature measurement unit 3 performs scanning.

Figure 8:
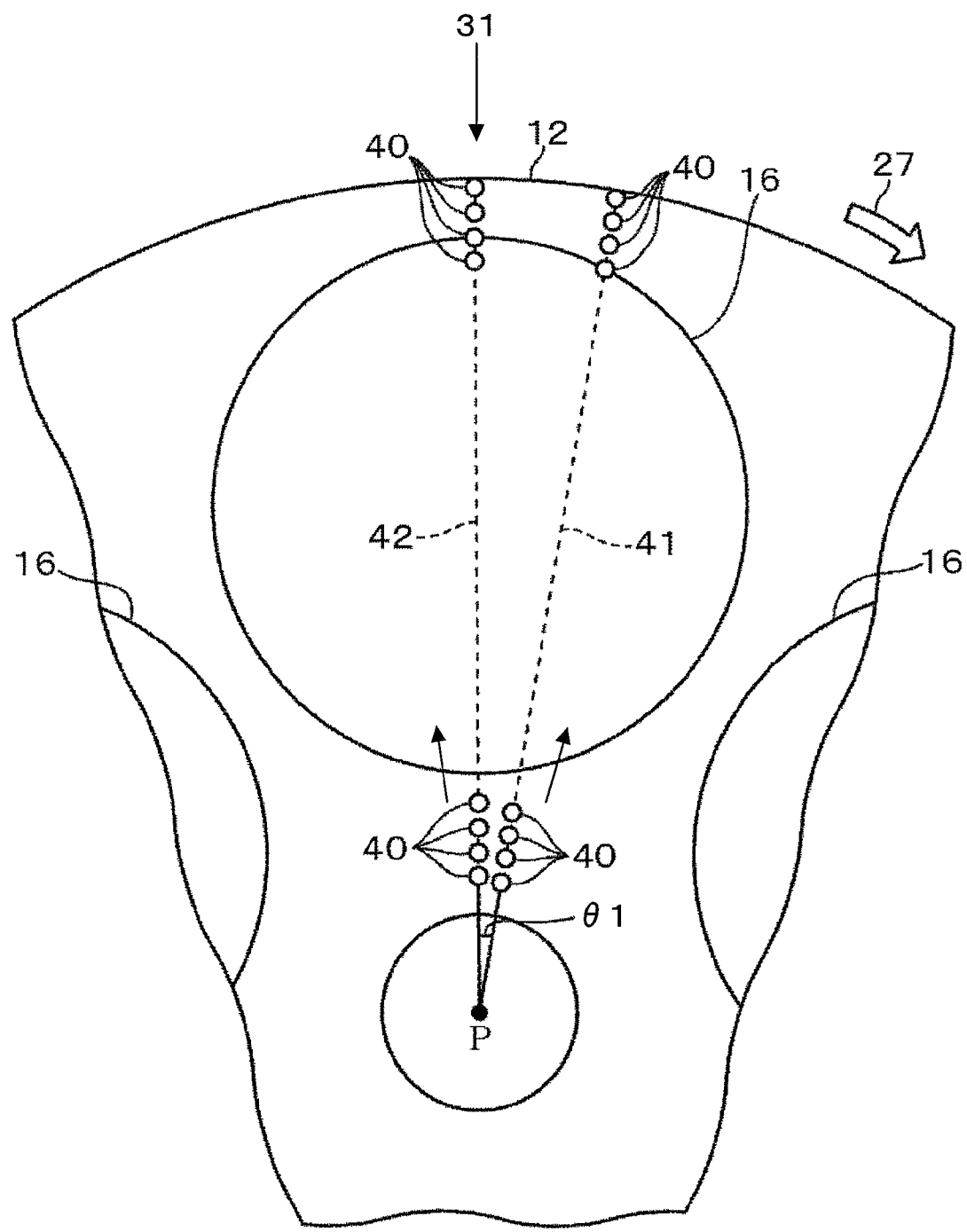
FIG. 8 is a schematic view showing temperature measurement areas.

FIG. 8 is a schematic view showing a relationship between the rotating table 12 and the temperature measurement areas 40.

The radiation temperature measurement unit 3 scans the rotating table 12 below the slit 31 of the top plate 13 from the inner side to the outer side of the rotating table 12 in the radius direction of the rotating table 12.

For example, when it is assumed that an area of the rotating table 12 shown by a line 41 is positioned below the slit 31 of the top plate 13 in "n"th ("n" is an integer) scanning, the radiation temperature measurement unit 3 scans the rotating table 12 on the line 41 from the inner side to the outer side to measure the temperature of the plural temperature measurement areas 40. Subsequently, when it is assumed that the rotating table 12 is rotated in a direction shown by an arrow 27, an area of the rotating table 12 shown by a line 42 is positioned below the slit 31 of the top plate 13 in "n+1"th ("n" is an integer) scanning. At this time, the radiation temperature measurement unit 3 scans the rotating table 12 on the line 42 from the inner side to the outer side to measure the temperature of the plural temperature measurement areas 40. FIG. 8 shows this status.

As described above, when the detection unit 301 is configured to absorb the infrared ray for 128 times by each of the reflection planes 303 to 305 of the rotating body 302 while the rotating body 302 is being rotated, there exist 128 temperature measurement areas 40 on each of the lines 41 and 42.

By the rotation of the rotating table 12, the lines 41 and 42 are shifted for an angle corresponding to the rotation speed of the rotating table 12 while having a rotation center "P" as the center. As described above, by repeating the scanning while rotating the rotating table 12, the measured temperature values of the plural areas at the surface of the rotating table 12 can be obtained.

With this, the temperature at the plural areas at the surface of the rotating table 12 in the circumferential direction can be measured by the radiation temperature measurement unit 3.

In this embodiment, the temperature profile in the vacuum chamber 11 of the film deposition apparatus 1 is measured by measuring the temperature of the surface of the rotating table 12. This process is explained in the following.

In this embodiment, the rotating table 12 may be composed of a material on which a temperature profile the same as that formed in the vacuum chamber 11 is generated when the vacuum chamber 11 is heated by the heater 20, such as quartz or the like, for example. Here, "the surface of the rotating table 12" includes the status where the wafers W are mounted on the concave portions 16 of the rotating table 12.

First, while the rotating table 12 is kept immobile, the vacuum chamber 11 is heated by the heater 20. With this, a temperature profile is generated in the vacuum chamber 11. Here, the rotating table 12 is kept immobile for a predetermined period. With this, a temperature profile which is the same as that generated in the vacuum chamber 11 is generated on the surface of the rotating table 12. Then, while the temperature profile is kept at the surface of the rotating table 12 by its heat capacity, the temperature of the surface of the rotating table 12 is scanned by the radiation temperature measurement unit 3 to measure the temperature profile. It means that the temperature at the surface of the rotating table 12 is measured because it is assumed that the temperature profile in the vacuum chamber 11 coincides with the temperature profile at the surface of the rotating table 12. Here, the rotation speed of the rotating table 12 may be, 12 cycles/min, for example.

Figure 9:
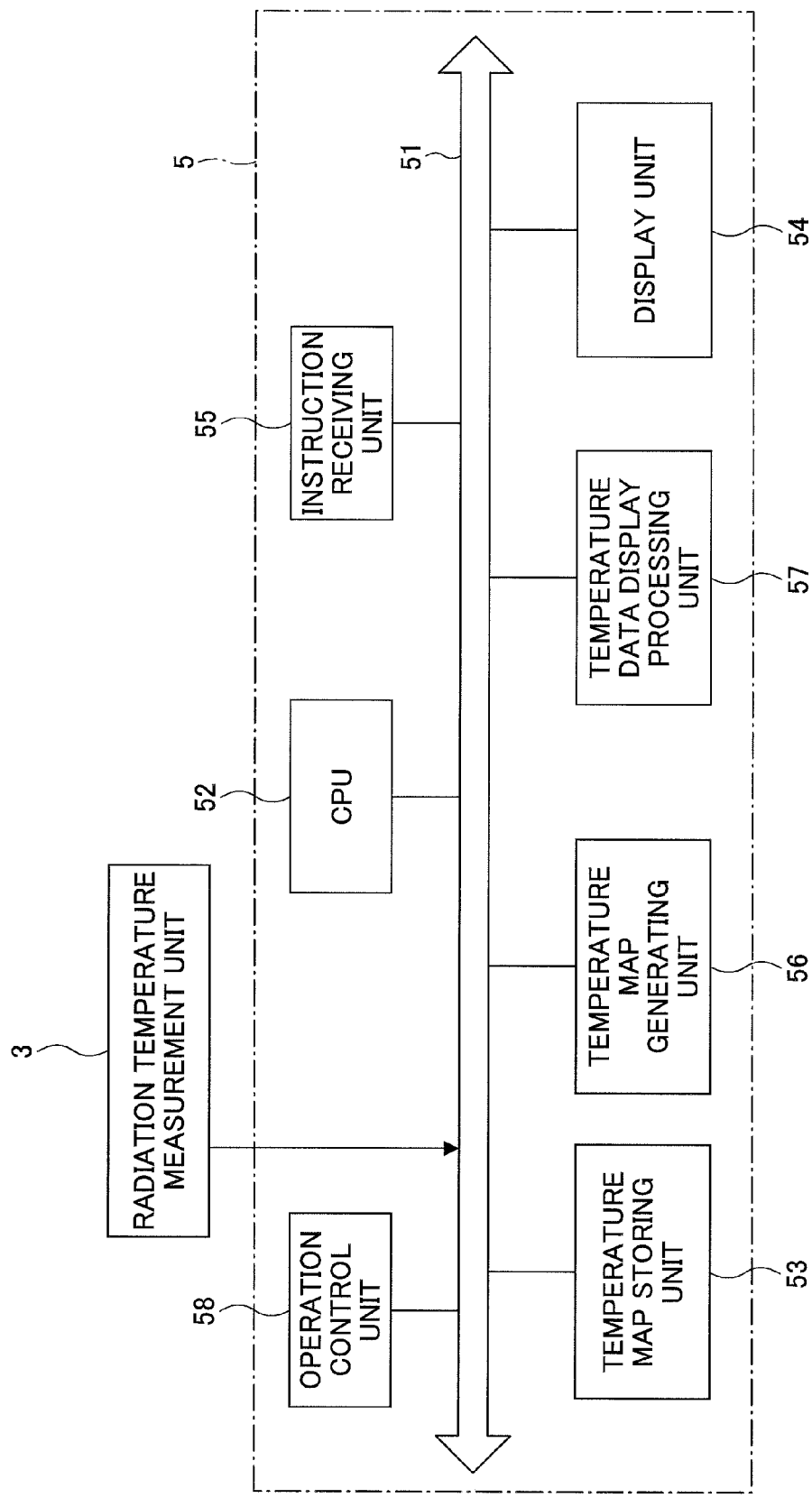
FIG. 9 is a block diagram of a control unit of the film deposition apparatus.

Next, the structure of the control unit 5, which is a computer provided to the film deposition apparatus 1, is explained with reference to a block diagram shown in FIG. 9.

The control unit 5 includes a bus 51, a CPU 52, a temperature map storing unit 53, a display unit 54, an instruction receiving unit 55, a temperature map generating unit 56, a temperature data display processing unit 57, and an operation control unit 58. Here, the instruction receiving unit 55, the temperature map generating unit 56, the temperature data display processing unit 57, and the operation control unit 58 correspond to functional blocks of the control unit 5 which are actualized by the CPU 52 and programs executed by the CPU 52. Although not shown in the drawings, the control unit 5 includes a storing unit that stores these programs.

The radiation temperature measurement unit 3, the CPU 52, the temperature map storing unit 53, the display unit 54, the instruction receiving unit 55, the temperature map generating unit 56, the temperature data display processing unit 57 and the operation control unit 58 are connected to the bus 51. The temperature map storing unit 53 is a memory that stores temperature map data (temperature data) in which addresses (positions) of the rotating table 12 and the measured temperature values correspond with each other, as will be explained later.

The display unit 54 displays image data indicating the temperature profile at the surface of the rotating table 12, graph data indicating a relationship between the addresses of the rotating table 12 in the radius direction and the temperature, graph data indicating a relationship between an average temperature value of the rotating table 12 at a certain angle and time, or the like.

The instruction receiving unit 55 receives an instruction from a user based on a predetermined operation by the user. In this embodiment, the instruction receiving unit 55 also functions as a display style selection receiving unit that receives a selection of a display style for data related to the temperature profile. Here, the display style may include a style in which a color image of a color spot corresponding to the temperature at the surface of the rotating table 12, a style in which a graph indicating a relationship between the addresses of the rotating table 12 in the radius direction and the temperature, a style in which a graph indicating a relationship between an average temperature value of the rotating table 12 at a certain angle and time, or the like.

The temperature map generating unit 56 may be actualized by a program that generates a temperature map based on the above described measured temperature values obtained from the radiation temperature measurement unit 3.

The temperature data display processing unit 57 may be actualized by a program capable of displaying the above described styles.

For the programs for actualizing the temperature map generating unit 56 and the temperature data display processing unit 57, steps or orders are embedded to be capable of instructing to generate the temperature map, display the data on the display unit 54 or the like.

The operation control unit 58 controls operations of components of the film deposition apparatus 1. In this embodiment, the operation control unit 58 may be actualized by a program in which steps or orders for controlling the operations of the components for measuring the temperature profile in the vacuum chamber 11 of the film deposition apparatus 1 are embedded.

These programs (including programs related to an input operation of process parameters and a display) are stored on a computer recording medium such as a flexible disk, a compact disk, a hard disk, a magneto-optical disk (MO), a memory card or the like, for example, and are installed in the control unit 5.

Figure 10:
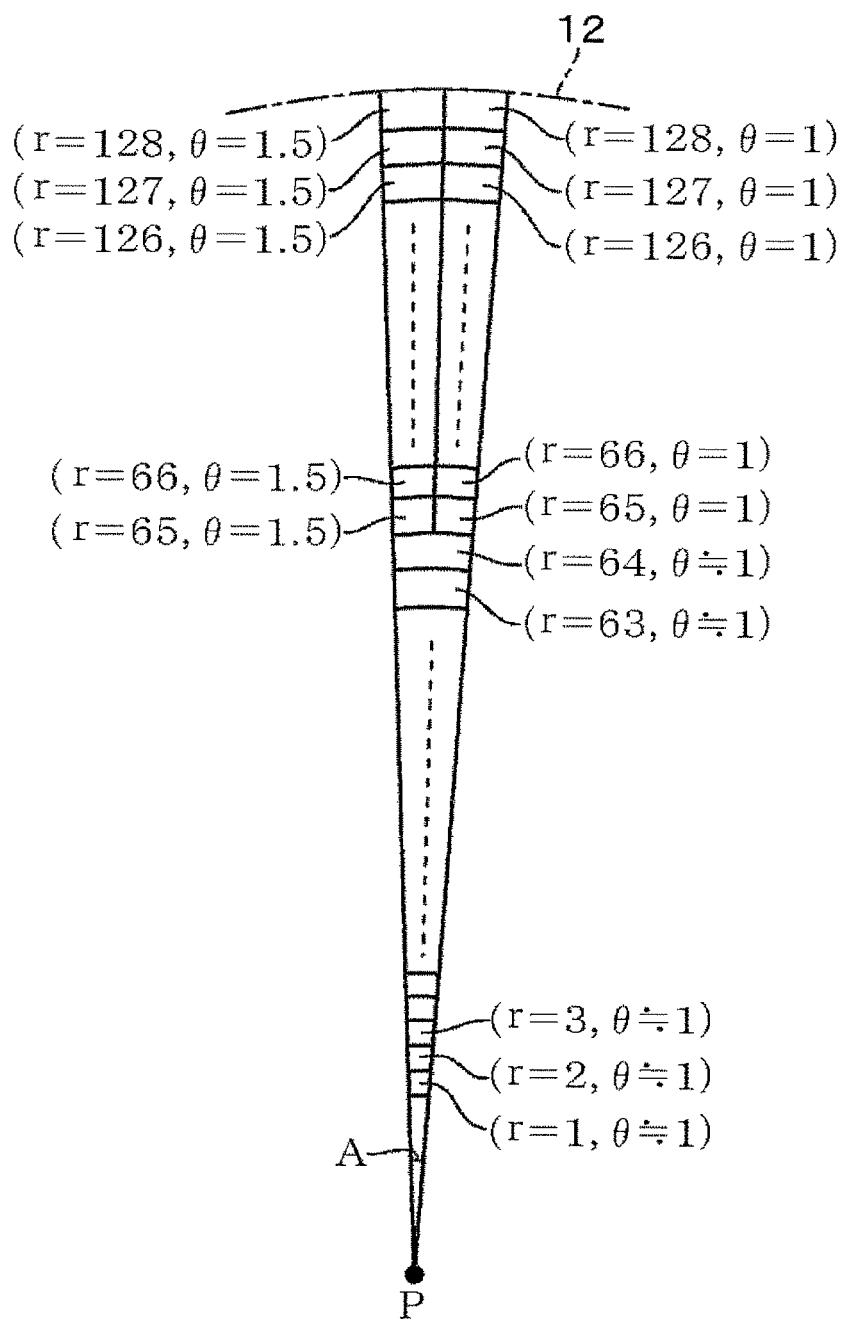
FIG. 10 is a schematic view showing addresses of a rotating table.

The addresses allocated to the surface of the rotating table 12 for generating the temperature map data are explained. FIG. 10 shows an example.

The addresses are defined by a polar coordinate composed of a radius coordinate "r" that specifies a position of the rotating table 12 in the radius direction and an angle coordinate "θ" that specifies the position of the rotating table 12 in the circumferential direction. The temperature map generating unit 56 generates the temperature map data by coordinating the measured temperature value obtained by the radiation temperature measurement unit 3 for each of the temperature measurement areas 40 with the address corresponding to the temperature measurement area 40. As described above, the radiation temperature measurement unit 3 detects the temperature of 128 areas in the radius direction in single scanning. Thus, for the radius coordinates "r" of the temperature measurement areas 40, values 1 to 128 are allocated. When the value of the radius coordinate "r" is small, it means that the corresponding temperature measurement area 40 is positioned at the inner side of the rotating table 12.

Further in this embodiment, the addresses of the surface of the rotating table 12 in the circumferential direction may be set for every 0.5° (which will be referred to as a divided angle as well, hereinafter). It means that the angle coordinates are allocated for every 0.5° while having the rotation center P of the rotating table 12 as a center. Thus, for the angle coordinates "θ" of the temperature measurement areas 40, values of every 0.5 between 0 to 355.5 are allocated. The divided angle of 0.5° is just an example and is not limited so. The value of the angle coordinate "θ" becomes larger as it goes to the upper stream of the rotation direction of the rotating table 12. The area adjacent to that having the angle coordinate "θ" as θ=0 at a downstream of the rotation direction of the rotating table 12 has the angle coordinate "θ" as θ=355.5.

FIG. 10 shows addresses of the rotating table 12 where the radius coordinate "r" takes 1 to 128 and the angle coordinate "θ" takes 1 and 1.5.

As shown in FIG. 10, when it is closer to the rotation center P, a distance between adjacent addresses of the rotating table 12 in the circumferential direction becomes shorter. Thus, the angle coordinates "θ" are allocated to take either of θ=1 and 1.5 at a range where the radius coordinate "r" is from 65 to 128, however, the angle coordinates "θ" are allocated to take only θ=1 at a range where the radius coordinate "r" is from 1 to 64. For areas other than θ=0.5 to 1, similarly, it is handled that the angle coordinates "θ" are allocated to take θ=m even when θ=m+0.5 ("m" is integer) at a range where the radius coordinate "r" is from 1 to 64. Here, in FIG. 10, the angle "A" is shown to be larger than it actually should be (1°) for explanation.

Figure 11:
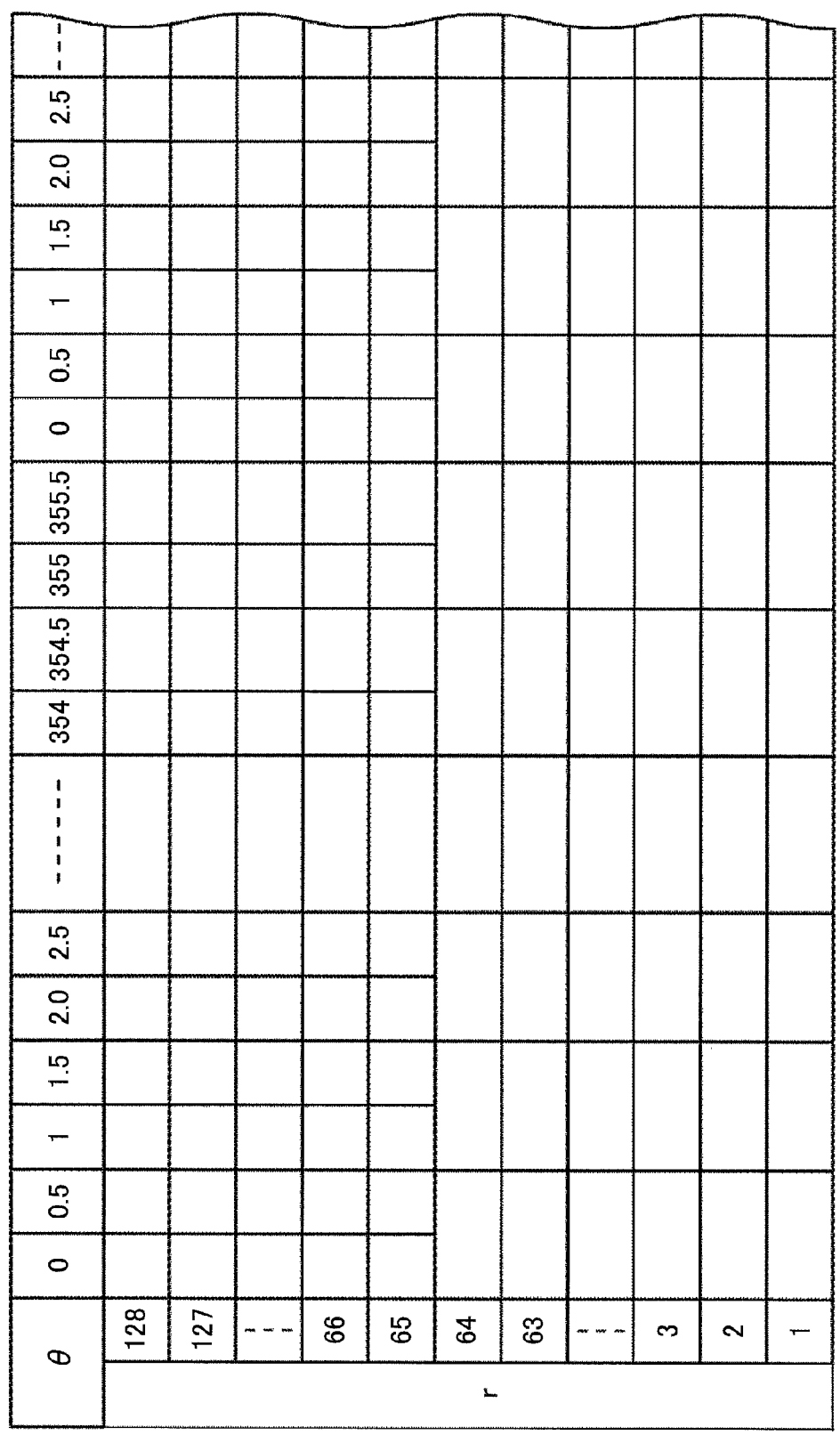
FIG. 11 is a diagram showing an example of a structure of temperature map data stored in a temperature map storing unit.

FIG. 11 is a diagram showing an example of a structure of the temperature map data stored in the temperature map storing unit 53.

In the temperature map data, the measured temperature value detected by the radiation temperature measurement unit 3 corresponds with a region specified by the address (r, θ) which is in accordance with the temperature measurement area 40 where the measured temperature value is obtained.

The correspondence of the temperature measurement area 40 with the address (r, θ) is explained.

In this embodiment, the temperature map generating unit 56 is configured to obtain a clock signal of the control unit 5 and the rotation speed of the rotating table 12.

The temperature map generating unit 56 specifies the radius coordinate "r" by counting the number of the measured temperature values sent from the radiation temperature measurement unit 3 from the start of measurement, based on the clock signal of the control unit 5. For example, for the measured temperature value sent from the radiation temperature measurement unit 3 first after the measurement is started, the radius coordinate "r" becomes r=1, for the 125th measured temperature value sent from radiation temperature measurement unit 3, the radius coordinate "r" becomes r=125, and for the 225th measured temperature value sent from radiation temperature measurement unit 3, the radius coordinate "r" becomes r=225−128=97.

The temperature map generating unit 56 specifies the angle coordinate "θ" based on the clock signal of the control unit 5 and the rotation speed of the rotating table 12.

For example, for the measured temperature values sent from the radiation temperature measurement unit 3 in a first scanning operation after the measurement is started, the angle coordinate "θ" becomes θ=0. Here, θ=0 means a position where the slit 31 is provided, as explained with reference to FIG. 3 and FIG. 4.

Then, the temperature map generating unit 56 specifies the angle coordinate "θ" for the measured temperature values sent from the radiation temperature measurement unit 3 in the next scanning operation based on the clock signal of the control unit 5 and the rotation speed of the rotating table 12.

It means that when it is assumed that the generation of the temperature map data is performed for 1 minute and the rotation speed of the rotating table 12 is 12 cycles/min, 12 groups of temperature map data for 0° to 360° can be continuously obtained. Thus, the temperature map data in accordance with a time from the starting of the measurement can be obtained. Here, as will be explained later, in this embodiment, the scanning speed of the radiation temperature measurement unit 3 is sufficiently fast compared with the rotation speed of the rotating table 12. Therefore, the measured temperature values obtained in the same scanning operation are handled to be obtained at the same time when displaying the measured temperature values as a graph or the like.

Figure 12:
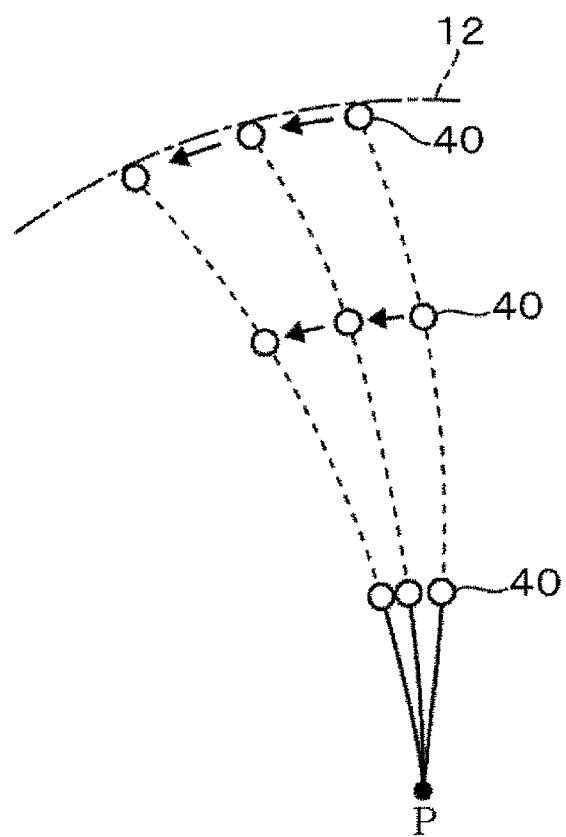
FIG. 12 is a plan view showing the temperature measurement areas.

Here, as the scanning operation by the radiation temperature measurement unit 3 is performed while the rotating table 12 is being rotated, actually, the temperature measurement areas 40 shift like a curve toward an upper stream of the rotation direction of the rotating table 12 while the temperature measurement areas 40 are shifted from the inner side to the outer side of the rotating table 12 in a single scanning operation, as shown in FIG. 12.

However, in this embodiment, a curved amount is not so significant so that the temperature map generating unit 56 is configured to handle that the temperature measurement areas 40 are shifted in a straight line in the radius direction of the rotating table 12 in a single scanning operation as shown in FIG. 4. It means that the temperature map generating unit 56 generates the temperature map data while handling the angle coordinates "θ" for the measured temperature values obtained in a single scanning operation as the same and the angle coordinates "θ" for the radius coordinates "r" of r=2 to 128 in the single scanning operation are the same as that for the radius coordinate "r" of r=1.

Here, as the rotation speed of the rotating table 12 when measuring the temperature is 12 cycles/min as described above, an angle θ1 by the chain lines 41 and 42 shown in FIG. 8 becomes 0.48° which is calculated based on the following equation 1.

$$\theta 1 = \text{"rotation times (cycles or revolutions) of the rotating table \textbf{12} per second (cycles/sec)"} \times 360°/\text{"scan speed (Hz)"} = 12/60 \times 360 \times 1/150 = 0.48° \quad \text{(equation 1)}$$

Thus, when a single scanning operation is performed, for the next scanning, the value of the angle coordinate "θ" is increased for 0.48° with respect to that of the current scanning so that the measured temperature values are corresponded in regions specified by the addresses with the increased value of "θ". As described above, in this embodiment, the divided angle for the angle coordinate "θ" is set as 0.5°. Thus, when the value of "θ" cannot be divided by 0.5, the control unit 5 may approximate the value of "θ" to a value nearest to the original value among values capable of being divided by 0.5.

Further, by approximating the value of "θ" as described above, there may be a case where the values of "θ" for the "n"th scanning operation and the (n+1)th scanning operation are the same. In such a case, either of the values may be used.

Further, although it is described in the above that the angle coordinates "θ" are set for every 0.5° while having the rotation center P of the rotating table 12 as a center, the divided angle may be set to the angle θ1 which is calculated based on the rotation speed of the rotating table 12 and the scanning speed of the radiation temperature measurement unit 3 as shown by the equation 1 (for example 0.48°).

An example of an operation of measuring the temperature profile in the vacuum chamber 11 by the film deposition apparatus 1 is explained.

For example, when performing the operation of measuring the temperature profile in the vacuum chamber 11, the rotating table 12 is kept immobilized. In this example, similar to when depositing layers on the wafers, five wafers W are mounted on the concave portions 16 of the rotating table 12. Then, under this status, a user performs a predetermined operation using an operation unit (not shown in the drawings) to switch on the heater 20. The instruction receiving unit 55 receives an instruction by the user. The operation control unit 58 switches on the heater 20 while immobilizing the rotating table 12 based on the instruction received by the instruction receiving unit 55 to start heating. With this, the temperature of the heater 20 is raised and an output of the heater becomes constant over time. When the output of the heater 20 becomes constant, the temperature of the rotating table 12 is stabilized so that a temperature profile in accordance with a temperature profile in the vacuum chamber 11 is generated on the surface of the rotating table 12 (and the surfaces of the wafers W).

After a predetermined period has passed from the start of heating, the user performs a predetermined operation by the operation unit (not shown in the drawings) to instruct to measure the temperature of the surface of the rotating table (and the surfaces of the wafers W). The instruction receiving unit 55 receives the user's instruction. Based on the instruction received by the instruction receiving unit 55, the operation control unit 58 controls the rotating table 12 to be rotated at a predetermined rotation speed, for example, 12 cycles/min. At the same time, the operation control unit 58 controls the radiation temperature measurement unit 3 to perform repeated scanning operations from the inner side to the outer side of the rotating table 12 in the radius direction to measure the temperature of the surface of the rotating table 12 (and wafer W). At this time, the temperature profile of the surface of the rotating table 12 is maintained by the heat capacity of the rotating table 12.

The temperature map generating unit 56 coordinates the measured temperature value measured by the radiation temperature measurement unit 3 to an address corresponding to the scanned temperature measurement area 40 to be stored in the temperature map storing unit 53 as the temperature map data.

In this embodiment, the operation control unit 58 controls to terminate the rotation of the rotating table 12, the scanning operation by the radiation temperature measurement unit 3 and the generation of the temperature map data by the temperature map generating unit 56, when the rotating table 12 is rotated one cycle (360°.

Figure 13:
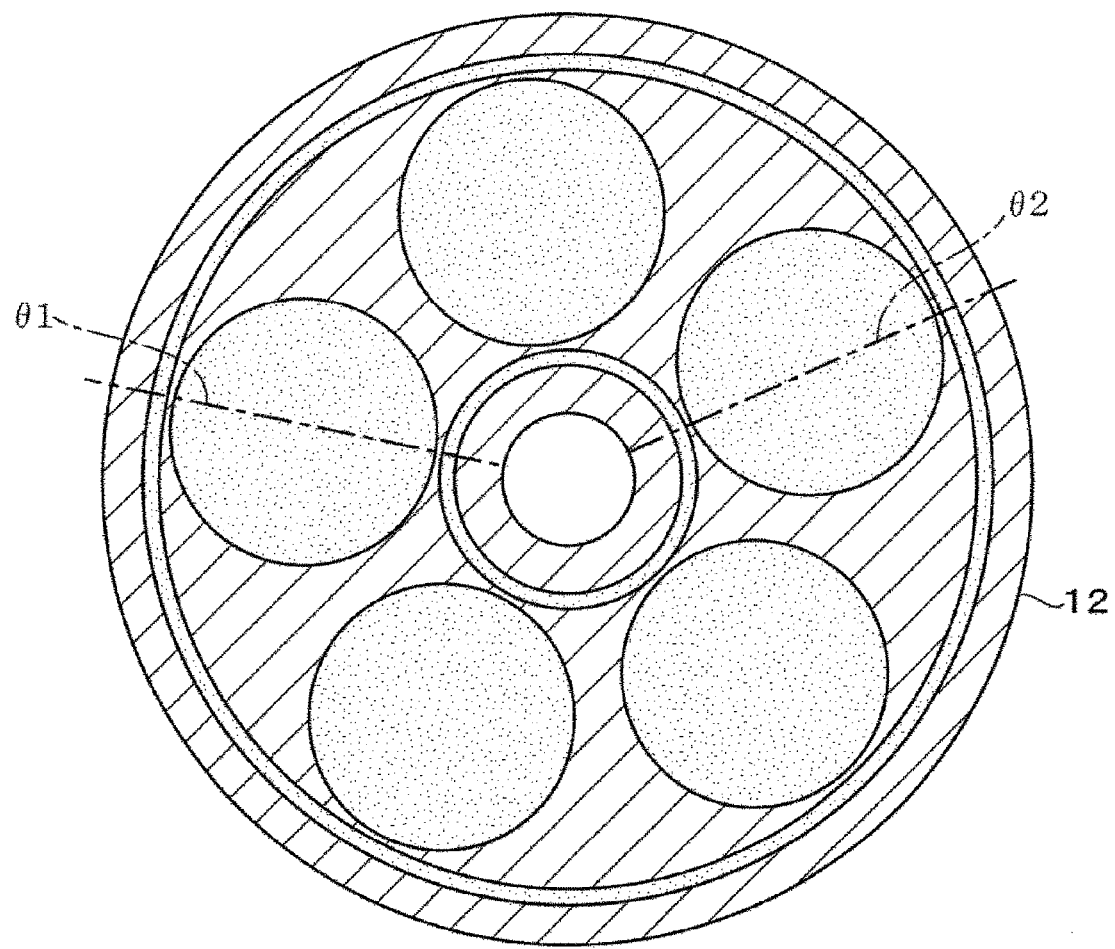
FIG. 13 is a schematic view showing a temperature profile of the rotating table displayed on a display unit.
Figure 14:
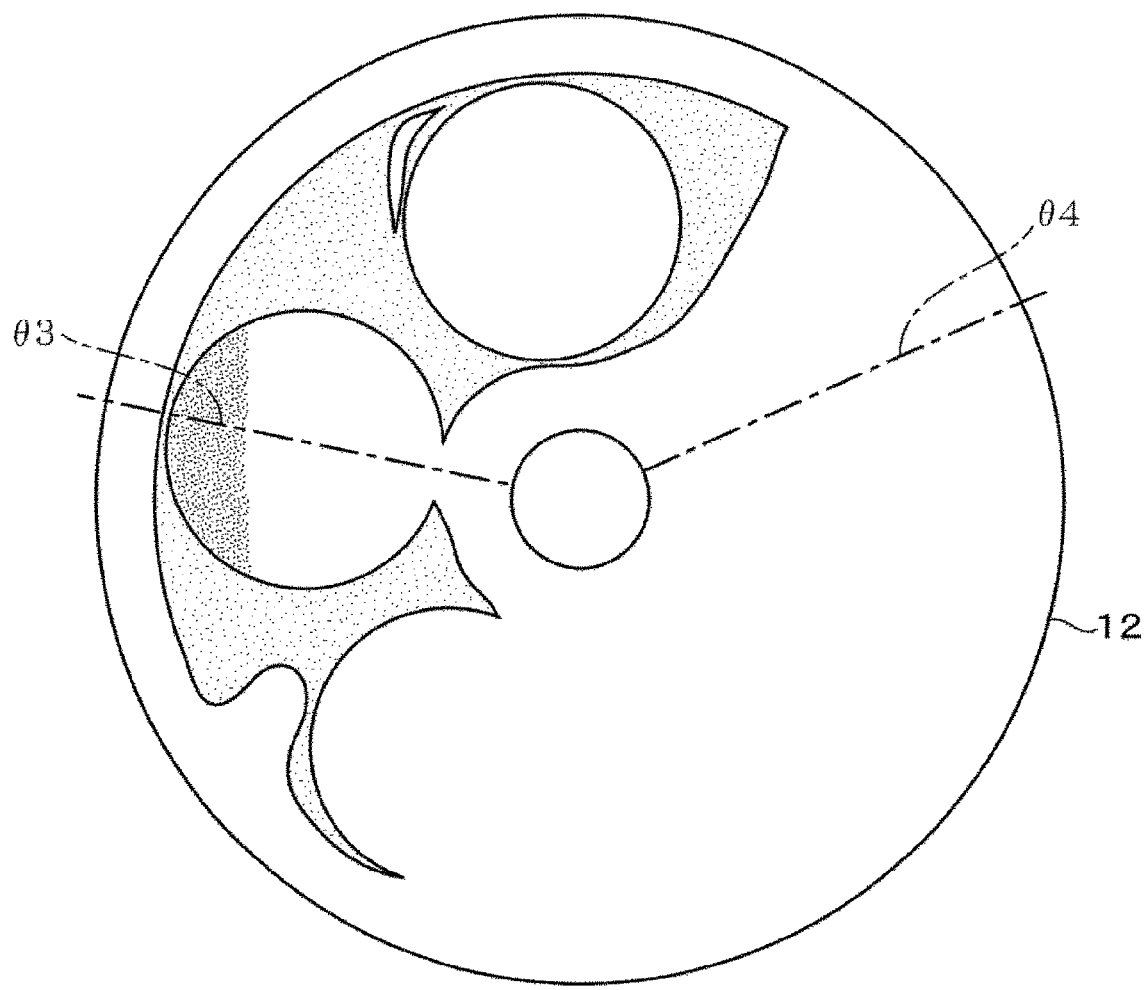
FIG. 14 is a schematic view showing a temperature profile of the rotating table displayed on a display unit.

The temperature data display processing unit 57 refers to the temperature map data stored in the temperature map storing unit 53 to display the measured temperature values of the scanned temperature measurement areas 40 as color spots, in accordance with the measured temperature values on the display unit 54. With this, by an assembly of the color spots, a color image of the rotating table 12 is displayed on the display unit 54. Specifically, when the instruction receiving unit 55 receives an instruction from a user, the temperature profile of the rotating table 12, in other words, the temperature profile in the vacuum chamber 11 in a plan view is shown as a color image. FIG. 13 and FIG. 14 are schematic views of a color image obtained by measuring the temperature profile of the rotating table 12 while changing the output of the heater 20. These color images are shown by a gray-scale gradation for explanation in FIG. 13 and FIG. 14. Here, the temperature is higher in this order: dense gray>diluted gray>hatched area in FIG. 13 and FIG. 14.

Here, for the measured temperature values having the same angle coordinate "θ", as the value of "r" of the radius coordinate becomes larger, it is shown as color spots at the outer periphery side of the rotating table 12. As explained above with reference to FIG. 12, by the rotation of the rotating table 12, the temperature measurement areas 40 shift like a curve toward an upper stream of the rotation direction of the rotating table 12 while the temperature measurement areas 40 are shifted from the inner side to the outer side of the rotating table 12 in a single scanning operation. Thus, in this embodiment, the temperature data display processing unit 57 handles that the temperature measurement areas 40 are shifted on a curved line which curves toward the upper stream of the rotation direction while the temperature measurement areas 40 are shifted from the inner side to the outer side of the rotating table 12 in a single scanning operation. With this, an actual temperature profile in the vacuum chamber 11 can be accurately displayed on the display unit 54. The amount of curve may be determined based on the rotation speed of the rotating table 12 when measuring the temperature so that the positions of the measured temperature values substantially correspond with output positions of the color spots, respectively.

Alternatively, the temperature data display processing unit 57 may handle that the temperature measurement areas 40 are shifted in a straight line in the radius direction of the rotating table 12 in a single scanning operation.

Other display styles to be displayed on the display unit 54, in addition to the color image of the rotating table 12 are explained. When a user appoints an arbitrary straight line extending in the radius direction on the color image of the rotating table 12, the temperature data display processing unit 57 displays a graph indicating a temperature profile of the straight line of the rotating table 12 on the display unit 54.

Figure 15:
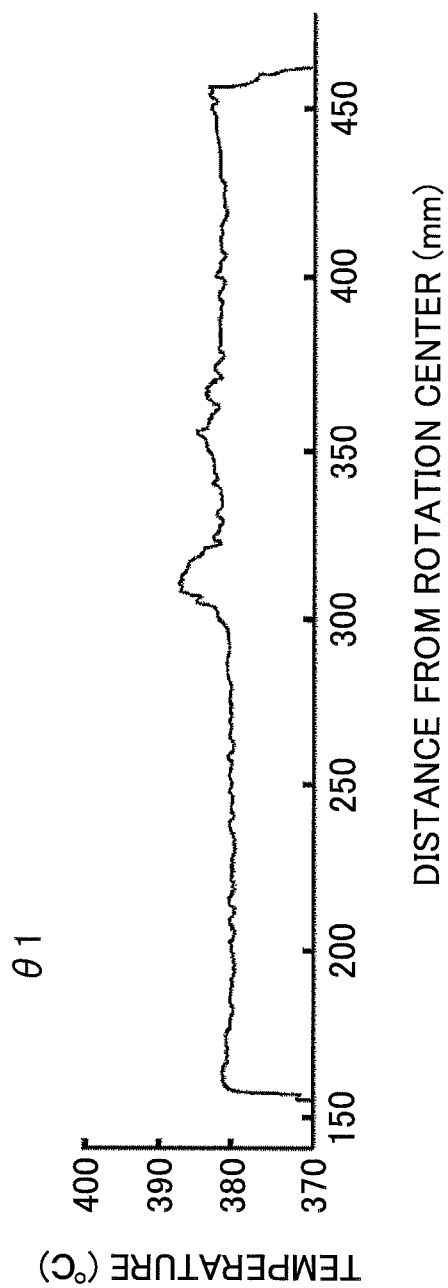
FIG. 15 is a graph showing a relationship between positions of the rotating table in a radius direction and temperature.
Figure 16:
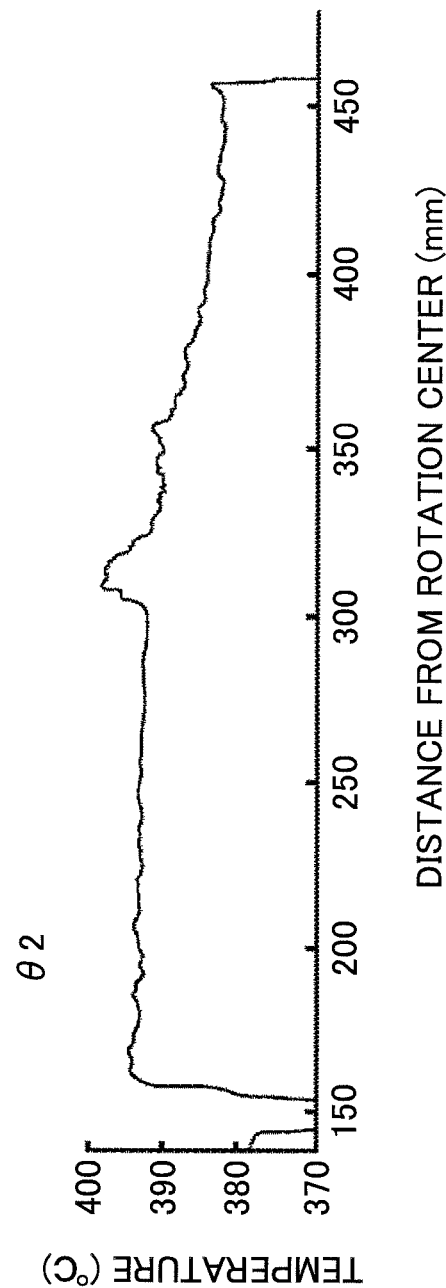
FIG. 16 is a graph showing a relationship between positions of the rotating table in a radius direction and temperature.
Figure 17:
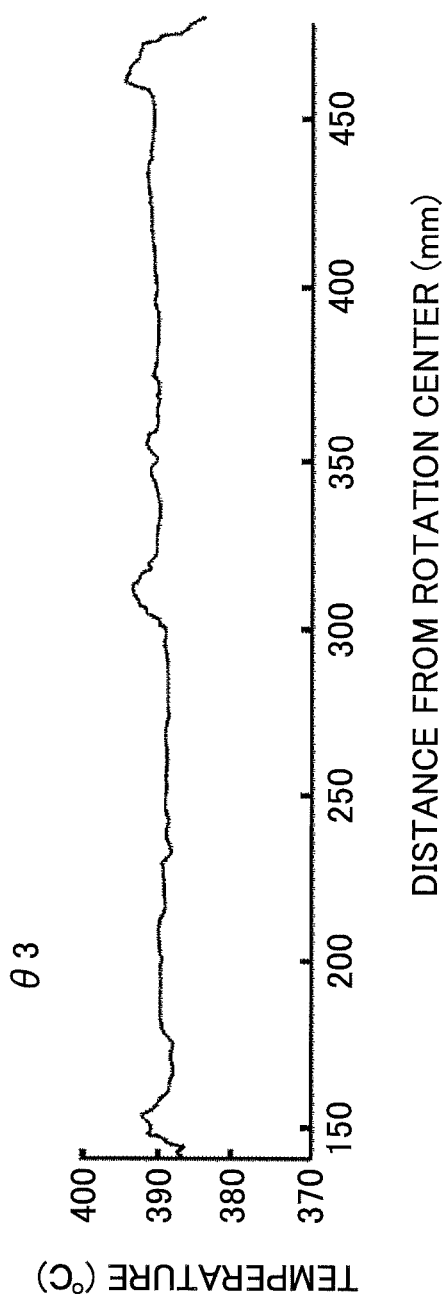
FIG. 17 is a graph showing a relationship between positions of the rotating table in a radius direction and temperature.
Figure 18:
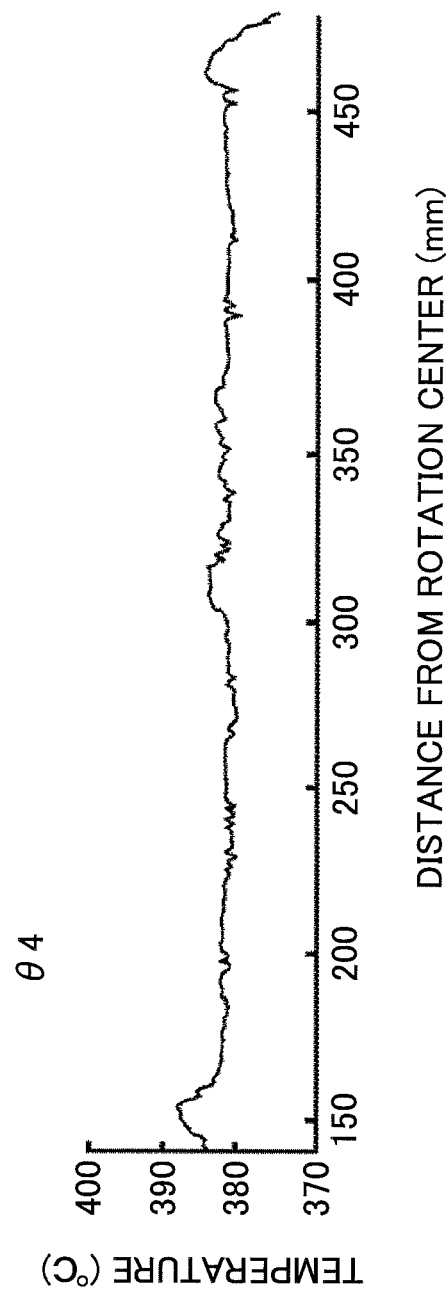
FIG. 18 is a graph showing a relationship between positions of the rotating table in a radius direction and temperature.

FIG. 15 and FIG. 16 show examples of graphs when the user appoints areas shown as θ1 and θ2 in FIG. 13. FIG. 17 and FIG. 18 show examples of graphs when the user appoints areas shown as θ3 and θ4 in FIG. 14. Here, it is assumed that θ1 and θ3 are the same area and θ2 and θ4 are the same area. The abscissa axis for each of the graphs is a distance from the rotation center P (mm) where the distance is set in correspondence with the radius coordinate "r". The ordinate axis of each of the graphs is the temperature (° C.).

A method of forming the graph is explained. The user appoints the area of a line. As described above, as the temperature data display processing unit 57 handles that the temperature measurement areas 40 are shifted on the curved line, the measured temperature values for which the values of the angle coordinates "θ" are displayed on the line in this embodiment. However, the temperature data display processing unit 57 may output the measured temperature values having the angle coordinates "θ" same as that of the measured temperature value of the most inner side of the appointed area of line. Then, the temperature data display processing unit 57 generates a graph of the measured temperature values of the temperature measurement areas 40 having the above angle coordinates "θ" and the radius coordinates "r" of r=1 to 128.

Alternatively, the temperature data display processing unit 57 may output the measured temperature values having the angle coordinates "θ" shifted as the radius coordinate "r" increases.

According to the film deposition apparatus 1 of the embodiment, the temperature profile generated in the vacuum chamber 11 is reflected onto the surface of the rotating table 12 by immobilizing the rotating table 12 for a predetermined period. Then, the temperature of the surface of the rotating table 12 are measured by repeatedly scanning the surface of the rotating table 12 along the radius direction by the radiation temperature measurement unit 3 while rotating the rotating table 12 for one cycle (revolution) while the rotating table 12 maintains the temperature profile.

Further, the temperature map generating unit 56 is configured to grasp the clock signal of the control unit 5 and the rotation speed of the rotating table 12. The temperature map generating unit 56 coordinates the measured temperature values obtained by the radiation temperature measurement unit 3 with addresses of the rotating table 12 (positions in the vacuum chamber 11) to store them in the temperature map storing unit 53 as temperature map data.

Specifically, the temperature map generating unit 56 coordinates the measured temperature value which is obtained by the radiation temperature measurement unit 3 first with an inner side position (for example, r=1) of the rotating table 12 and where the slit 31 is provided (e=0), and obtains 128 measured temperature values from that position (including that position) as the measured temperature values having the angle coordinate "θ" of θ=0 while the radius coordinate "r" is increased. Then, the temperature map generating unit 56 coordinates the 129th measured temperature value with the next angle coordinate "θ" (for example, θ=0.5° in a direction opposite to the rotating direction of the rotating table 12, at the inner side position (for example, r=1) of the rotating table 12. Then, from that position toward the outer side, the temperature map generating unit 56 obtains 128 measured temperature values (including that position) as the measured temperature values having the angle coordinate "θ" of θ=0.5 while the radius coordinate "r" is increased. This operation is repeated for a cycle of the rotating table 12.

The temperature data display processing unit 57 displays the temperature profile of the surface of the rotating table 12 on the display unit 54 based on the temperature map data stored in the temperature map storing unit 53.

With the above structure, a user can estimate the temperature profile in the vacuum chamber 11 in detail based on a color image of the rotating table 12 or a graph shown on the display unit 54.

As described above, according to the film deposition apparatus 1 of the embodiment, it is not necessary to attach the thermocouples in the vacuum chamber 11. Further, it is not necessary to open the vacuum chamber 11 to the atmosphere for attaching the thermocouples. Therefore, the temperature profile generated in the vacuum chamber 11 can easily be predicted.

The measurement of the temperature profile may be performed in developing the apparatus, at a maintenance period for the apparatus between processing to the wafers W for confirming the operation of the apparatus.

Further, in the above embodiment, although the temperature of the plural areas of the rotating table 12 is measured by repeatedly performing the scanning operation while the rotating table 12 is rotated for one cycle at a relatively slow speed, the temperature of the plural points of the rotating table may be measured by repeatedly performing the scanning operation while rotating the rotating table 12 at a faster speed.

Further, the above measurement of the temperature profile may be performed where the wafers W are not mounted on the rotating table 12.

Further, when the wafers W are mounted on the concave portions 16 of the rotating table 12, there is a possibility that the heat conductivity or the heat capacity may be different from the material composing the wafers W and the material composing the rotating table 12. Therefore, the temperature map generating unit 56 may correct the measured temperature values measured by the radiation temperature measurement unit 3 based on the used materials.

For example, the temperature map generating unit 56 may correlate the measured temperature values of the temperature measurement areas 40 corresponding to the positions of the concave portions 16 of the rotating table 12 with respect to the measured temperature values of the temperature measurement areas 40 of the positions of the rotating table 12 other than the concave portions 16. The temperature map generating unit 56 may store a temperature correction value for the positions of the rotating table 12 other than the concave portions 16 or a temperature correction value for the wafers W mounted on the concave portions 16 of the rotating table 12. Further, the positions corresponding to the concave portions 16 of the rotating table 12 may be detected by previously storing map data or the like in the control unit 5, or may be detected by a pattern matching or the like based on the measured temperature values measured by the radiation temperature measurement unit 3.

Further, when the wafers W are not mounted on the concave portions 16 of the rotating table 12, the height of the concave portions 16 are different from a part other than the concave portions 16. Therefore, in order to compensate the difference in height, the correction may be performed in this case as well.

Further, the operation for measuring the temperature profile in the vacuum chamber 11 by the film deposition apparatus 1 may be controlled by the operation control unit 58. When the instruction receiving unit 55 receives an instruction to start the measurement of the temperature profile from a user, the operation control unit 58 switches on the switch of the heater 20 to start heating while immobilizing the rotating table 12. Subsequently, when a predetermined set period has passed for the heater to become a predetermined temperature and the temperature of the rotating table 12 to become stable, the operation control unit 58 controls to start the rotation of the rotating table 12 and the scanning by the radiation temperature measurement unit 3.

Figure 19:
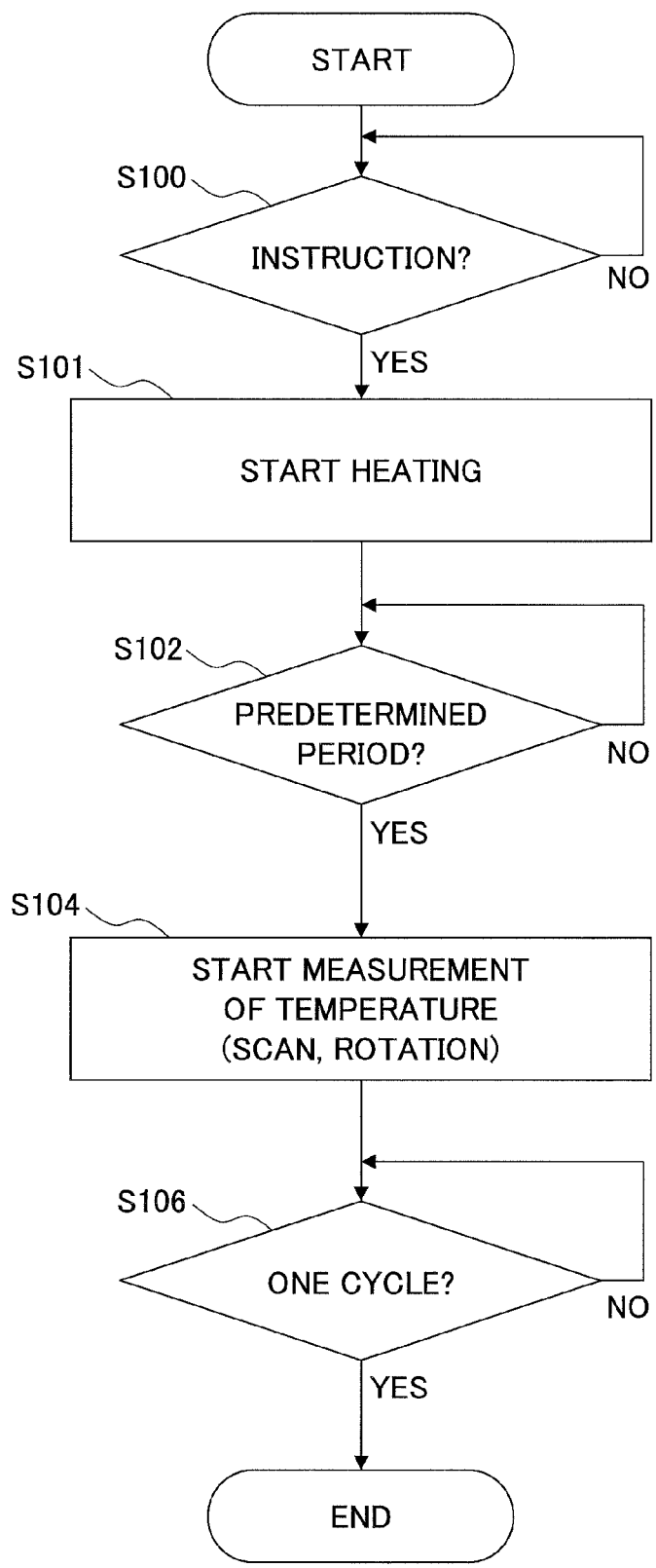
FIG. 19 is a flowchart showing an operation of an operation control unit.

FIG. 19 is a flowchart showing an operation of the operation control unit 58.

When an instruction to start a measurement of the temperature profile in the vacuum chamber 11 by a user is received (YES of step S100), the operation control unit 58 switches on the switch of the heater 20 to start heating of the vacuum chamber 11 (step S101). At this time, the rotating table 12 is not rotated. After a predetermined period from the start of heating (YES of step S102), the operation control unit 58 starts the scanning operation by the radiation temperature measurement unit 3 so that the scanning from the inner side to the outer side of the rotating table 12 and the rotation of the rotating table 12 are started (step S104). Here, the temperature map generating unit 56, based on the control by the operation control unit 58, stores the measured temperature values measured by the radiation temperature measurement unit 3 in correspondent with the addresses corresponding to the scanned temperature measurement areas 40 to generate the temperature map data.

The predetermined period necessary for the heater 20 to be stable and the rotating table 12 to generate the temperature profile reflecting the temperature profile in the vacuum chamber 11 after the heater 20 is switched on, may be previously obtained by a simulation or the like based on the kind of the heater 20, materials composing the rotating table 12 or the wafers W or the like and stored in the control unit 5.

Thereafter, when the operation for one cycle of the rotating table 12 is finished (YES of step S106), the measurement operation of the temperature profile in the vacuum chamber 11 by the film deposition apparatus 1 is finished.

Here, after the operation for one cycle (360°) of the rotating table 12 is finished, the same operation in which the rotating table 12 is immobilized for the predetermined period and after that the surface of the rotating table 12 is scanned for measuring the temperature, may be repeated. At this time, the position of the rotating table 12 with respect to the vacuum chamber 11 may be set at the same position as the previous operation when it is immobilized. Then, the temperature at the same positions as the previous operation may be measured to calculate average values. Alternatively, the temperature at the positions different from those of the previous operation may be measured to obtain the temperature of a larger number of temperature measurement areas 40.

Further, although it is assumed that the temperature profile of the vacuum chamber 11 is reflected onto the rotating table 12 in this embodiment, if a temperature profile of the rotating table 12 itself exists, the temperature profile in the vacuum chamber 11 cannot be accurately measured via the rotating table 12. Therefore, alternatively, in order to prevent influence by the temperature profile of the rotating table 12 itself, the position of the rotating table with respect to the vacuum chamber 11 when the rotating table is immobilized for the predetermined period may be changed for every operation where the operation for one cycle (360°) of the rotating table 12 is repeated for several times. Then, the average values may be calculated.

In the above embodiment, when displaying the data along the radius direction, it is assumed that the rotating table 12 is terminated in a period for a single scanning operation. As such, when the rotation speed of the rotation table 12 is sufficiently slower than the scanning speed of the radiation temperature measurement unit 3 so that the position of the rotating table 12 does not change largely in the single scanning operation, the address of the temperature measurement areas 40 may be determined regardless of the rotating table 12.

Further, in order to measure the temperature of the areas in as large a number as possible for accurately obtaining the temperature profile of the rotating table 12, the operation control unit 58 may control the rotation speed of the rotating table 12 based on the scanning speed of the radiation temperature measurement unit 3, such that the radiation temperature measurement unit 3 scans the surface of the rotating table 12 in the radius direction of the rotating table 12 greater than or equal to 10 times while the rotating table 12 is rotated for one cycle with respect to the radiation temperature measurement unit 3.

The temperature measurement apparatus of the embodiment is provided with a radiation temperature measurement unit that measures the temperature of plural temperature measurement areas while scanning in the radius direction of the rotating table and rotating the rotating table after the rotating table is immobilized so that the temperature of the rotating table is stabilized, and a data processing unit that displays the temperature profile of the surface of the rotating table. Therefore, the temperature profile in the process container can be easily and accurately measured based on the temperature profile of the surface of the rotating table.

The present invention is not limited to the specifically disclosed embodiments, and variations and modifications may be made without departing from the scope of the present invention.

The present application is based on Japanese Priority Application No. 2011-118372 filed on May 26, 2011, the entire contents of which are hereby incorporated herein by reference.

What is claimed is:

1. A temperature measurement apparatus for estimating a temperature profile in a process container of a heat treatment apparatus including the process container, in which a rotating table for mounting a substrate is provided, and a heater for heating the process container, comprising:
   a radiation temperature measurement unit configured to measure the temperature of plural temperature measurement areas on a surface of the rotating table in a radius direction of the rotating table by scanning the surface of the rotating table in the radius direction;
   an instruction receiving unit that receives an instruction for measuring the temperature profile in the process container;
   an operation control unit that
      controls to start heating of the process container by the heater while keeping the rotating table immobilized, when the instruction receiving unit receives the instruction for measuring the temperature profile in the process container, and
      controls to repeat a scanning operation, in which the radiation temperature measurement unit scans the surface of the rotating table in the radius direction to obtain the temperature of the plural temperature measurement areas in the radius direction while the rotating table is rotated in a circumferential direction of the rotating table with respect to the radiation temperature measurement unit, after a predetermined period has passed from starting the heating of the process container, for obtaining the temperature of the plural temperature measurement areas at the surface of the rotating table in the radius direction and the circumferential direction from the radiation temperature measurement unit;
   a temperature map generating unit that
      specifies the address of the temperature measurement area for which the operation control unit obtains the temperature based on the number of the temperature measurement areas obtained by the radiation temperature measurement unit for each of the scanning operations in the radius direction of the rotating table, and the rotating speed of the rotating table, and
      stores the temperature in correspondence with the corresponding address in a storing unit; and
   a temperature data display processing unit that displays the temperature profile of the surface of the rotating table based on the temperature and the address stored in the storing unit by the temperature map generating unit, as the temperature profile in the process container.

2. The temperature measurement apparatus according to claim 1,
   wherein the radiation temperature measurement unit is configured to measure the temperature of the plural temperature measurement areas along a radius of the rotating table by scanning the surface of the rotating table in the radius direction at a predetermined position at the process container, and
   the operation control unit repeats the scanning operation at least until the rotating table is rotated for one cycle with respect to the radiation temperature measurement unit, for obtaining the temperature of the plural temperature measurement areas at the surface of the rotating table in the radius direction and the circumferential direction from the radiation temperature measurement unit.

3. The temperature measurement apparatus according to claim 1,
wherein, when the instruction receiving unit receives a predetermined angle of the rotating table, the temperature data display processing unit displays the temperature profile of a line along the predetermined angle based on the temperature and the addresses stored in the storing unit.

4. The temperature measurement apparatus according to claim 1,
wherein the operation control unit controls the rotation speed of the rotating table based on the scanning speed of the radiation temperature measurement unit, such that the radiation temperature measurement unit scans the surface of the rotating table in the radius direction of the rotating table greater than or equal to 10 times while the rotating table is rotated for one cycle with respect to the radiation temperature measurement unit.

5. The temperature measurement apparatus according to claim 1,
wherein the radiation temperature measurement unit measures the surface of the rotating table by receiving an infrared ray radiated from the surface of the rotating table,
the process container is provided with a slit at a predetermined position along an inner side to an outer side of the rotating table and a transparent plate which is configured to cover the slit as well as be capable of transmitting the infrared ray, and
the radiation temperature measurement unit measures the temperature of the plural temperature measurement areas along the radius direction of the rotating table by scanning the surface of the rotating table in the radius direction via the transparent plate.

6. The temperature measurement apparatus according to claim 1,
wherein the radiation temperature measurement unit is configured to scan the surface of the rotating table along the radius direction of the rotating table from an inner side to an outer side.

7. A heat treatment apparatus, comprising:
the process container in which the rotating table for mounting the substrate is provided;
the heater that heats the process container; and
the temperature measurement apparatus according to claim 1.

8. A method of estimating a temperature profile in a process container of a heat treatment apparatus including the process container, in which a rotating table for mounting a substrate is provided, and a heater for heating the process container, comprising:
starting heating of the process container by the heater while keeping the rotating table immobilized, based on an instruction for measuring the temperature profile in the process container;
after a predetermined period has passed from starting the heating of the process container, repeating a scanning operation, in which a radiation temperature measurement unit, which is configured to measure temperature of plural temperature measurement areas on a surface of the rotating table in a radius direction of the rotating table by scanning the surface of the rotating table in the radius direction, scans the surface of the rotating table in the radius direction to obtain the temperature of the plural temperature measurement areas in the radius direction while the rotating table is rotated in a circumferential direction of the rotating table with respect to the radiation temperature measurement unit;
specifying the address of the temperature measurement area for which the temperature is obtained based on the number of the temperature measurement areas obtained by the radiation temperature measurement unit for each of the scanning operations in the radius direction of the rotating table, and the rotating speed of the rotating table;
storing the temperature in correspondence with the corresponding address in a storing unit; and
displaying the temperature profile of the surface of the rotating table based on the temperature and the address stored in the storing unit, as the temperature profile in the process container.

9. The method of estimating a temperature profile according to claim 8,
wherein in the repeating the scanning operation, the scanning operation is repeated at least until the rotating table is rotated for one cycle with respect to the radiation temperature measurement unit, for obtaining the temperature of the plural temperature measurement areas at the surface of the rotating table in the radius direction and the circumferential direction from the radiation temperature measurement unit.

10. A non-transitory computer-readable recording medium having recorded thereon a program that causes a computer to execute the method of estimating a temperature profile according to claim 8.

* * * * *